(12) United States Patent
Komarova et al.

(10) Patent No.: US 8,912,139 B2
(45) Date of Patent: *Dec. 16, 2014

(54) PEPTIDE COMPOSITIONS AND METHODS FOR TREATING LUNG INJURY, ASTHMA, ANAPHYLAXIS, ANGIOEDEMA, SYSTEMIC VASCULAR PERMEABILITY SYNDROMES, AND NASAL CONGESTION

(71) Applicant: The Board of Trustees of the University of Illinois, Urbana, IL (US)

(72) Inventors: Yulia A. Komarova, Chicago, IL (US); Uzma Saqib, Chicago, IL (US); Stephen M. Vogel, Chicago, IL (US); Asrar B. Malik, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/230,642

(22) Filed: Mar. 31, 2014

(65) Prior Publication Data

US 2014/0213505 A1 Jul. 31, 2014

Related U.S. Application Data

(63) Continuation of application No. 14/105,385, filed as application No. PCT/US2012/042118 on Jun. 13, 2012.

(60) Provisional application No. 61/496,409, filed on Jun. 13, 2011.

(51) Int. Cl.
*A61K 38/17* (2006.01)
*C07K 7/08* (2006.01)
*C07K 7/06* (2006.01)
*C07K 14/705* (2006.01)
*A61K 47/48* (2006.01)
*A61K 38/00* (2006.01)

(52) U.S. Cl.
CPC ........ *A61K 47/48276* (2013.01); *A61K 38/1709* (2013.01); *A61K 38/00* (2013.01); *C07K 7/08* (2013.01); *C07K 7/06* (2013.01); *C07K 2319/033* (2013.01); *C07K 14/705* (2013.01); *C07K 2319/10* (2013.01)
USPC ............................ 514/1.7; 530/324; 514/21.3

(58) Field of Classification Search
CPC ....... A61K 38/00; A61K 38/08; A61K 38/03; A61K 38/04; C07K 14/705; C07K 2319/10
USPC .......................................................... 514/1.7
See application file for complete search history.

(56) References Cited

PUBLICATIONS

Q7UPK4 (UniProt, integrated Oct. 1, 2003).*
A6H8K3 (UniProt, integrated Jul. 24, 2007).*

* cited by examiner

*Primary Examiner* — James H Alstrum Acevedo
*Assistant Examiner* — Tara Martinez
(74) *Attorney, Agent, or Firm* — Polsinelli PC; Teddy C. Scott, Jr.; Ron Galant

(57) ABSTRACT

Provided herein are peptide inhibitors of the interaction between End Binding Protein 3 (EB3) and Inositol 1,4,5-Trisphosphate Receptor Type 3 (IP3R3). Also provided are methods and materials for treating lung injury, including acute lung injury, which may include hyperpermeability of lung vessels, vascular leakage, the development of edema, asthma, anaphylaxis, angioedema, systemic vascular permeability syndromes, and nasal congestion.

13 Claims, 21 Drawing Sheets

FIGURE 3

```
IP3R1isoform1    VTPVKYARLWSEIPSEIAIDD
IP3R1isoform2    VTPVKYARLWSEIPSEIAIDD
       IP3R2     VVPVRYARLWIEIPTKITIHE
       IP3R3     VTPVKFARLWTEIPTAITIKD
  EB binding     --------S/TxIP-------
```

SEQ ID NO: 1 IP3R3 peptide  KFARLWTEIPTAIT

EB3: Magenta
IP3R3 Peptide (KFARLWTEIPTAIT):
Green Ball n Stick
Zrank Score= -68.882 kcal/mole

US 8,912,139 B2

PEPTIDE COMPOSITIONS AND METHODS FOR TREATING LUNG INJURY, ASTHMA, ANAPHYLAXIS, ANGIOEDEMA, SYSTEMIC VASCULAR PERMEABILITY SYNDROMES, AND NASAL CONGESTION

STATEMENT OF GOVERNMENTAL INTEREST

This invention was made with government support under Grant Nos. RO1 HL045638 and RO1 HL103922 awarded by the National Institutes of Health. The government has certain rights in this invention.

FIELD OF THE INVENTION

The present invention relates to peptides for treating lung injury, including inflammation-mediated vascular leakage and the development of edema. The present invention also relates to treating asthma, anaphylaxis, angioedema, systemic vascular permeability syndromes, and nasal congestion using the peptides.

BACKGROUND

Microtubule (MT) cytoskeleton provides an important control-point of endothelial barrier regulation; however, the role of this key cytoskeleton element has not been well studied. The MT stabilizing drug taxol has been shown to attenuate the lung injury in mice models suggesting that MTs may be important in mediating increased lung vascular permeability. However, taxol displays a general toxicity that makes it an inconvenient drug for doctors and their patients.

Microtubule end binding proteins are highly conserved microtubule plus-end tracking accessory factors that bind to growing microtubules (MTs) and suppress MT catastrophic events. Two such end binding proteins, EB1 and EB3, play roles in regulating endothelial cytoskeletal dynamics and cell shape change, the primary determinants of the permeability of endothelial barrier.

Ca2+ is a highly versatile second messenger that regulates endothelial permeability and vascular homeostasis. The activation of phospholipase C β (PLCβ), downstream of PAR-1 activation mediates hydrolysis of phosphotidyl inositolbisphosphate (PIP2) into inositol 1,4,5-trisphosphate (IP3) and diacylglycerol (DAG). IP3 stimulates Ca2+ release from IP3-sensitive intracellular stores, i.e., the endoplasmic reticulum (ER). The depletion of Ca2+ from ER stores is mediated by activation of IP3R on the ER membrane and leads to transient increase in intracellular Ca2+. Ca2+ entry or "influx" is mediated by transient receptor potential canonical (TRPC) channels that are permeable to various cations including Ca2+ and Mg2+. TRPC1 and 4 are store-operated Ca2+ channels (SOC) in endothelial lung microvascular cells that are activated by depletion of ER.

The increase in intracellular concentration of Ca2+ upregulates activity of protein kinase Cα (PKC α). PKC α is a key regulator of the endothelial permeability response to multiple mediators 2. PKC α phosphorylates p120-catenin and mediates its dissociation from VE-cadherin, thus resulting in VE-cadherin internalization. PKC α also acts upstream of RhoA activation by phosphorylating p115RhoGEF and GDI-1. RhoA in turn facilitates phosphorylation-induced inhibition of myosin light chain phosphatase (MLCP) by activating Rho kinase (ROCK). The inhibition of MLCP is accompanied by the Ca2+/calmodulin-dependent activation of MLCK that leads to phosphorylation of MLC and induces acto-myosin contraction in response to pro-inflammatory mediators such as thrombin and histamine.

The integrity of MT cytoskeleton is required for IP3-induced Ca2+ release from ER stores. Alteration of MT dynamics by MT destabilizing or MT stabilizing agents nocodazole, colchicine and taxol inhibits IP3-gated release of Ca2+, suggesting that MT dynamics are required for full activation of IP3R. The MT cytoskeleton is involved in remodeling of ER, thus ensuring organization and propagation of Ca2+ waves in response to external stimuli. The ER attaches to and elongates together with MT growing ends though direct interaction of EB1 and EB3 with stromal interaction molecule 1 (STIM1). Depletion of EB1 in HeLa (HeLa cells do not express EB3) decreases ER protrusion events, however does not inhibit activation of SOC by thapsigargin suggesting that some other mechanisms are involved in activation of SOC and propogation of calcium signaling in epithelial cells. In endothelial cells, the localization of IP3R in caveolae is critical for both ER Ca2+ store depletion and SOC activation. This indicates that activation of IP3R and/or its responsiveness to IP3 is important element of calcium signaling. It is proposed that MT cytoskeleton positively regulates IP3R activation in response to IP3 and thus transmits extracellular signals throughout the cell, eliciting a physiological response.

Despite the advanced supportive care in the United States, about 100,000 patients die annually from Acute Lung Injury (ALI), a complex inflammatory response associated with neutrophil infiltration and release of cytokine and pro-inflammatory mediators during sepsis. Hyper-permeability of lung vessels, a characteristic feature of the disease, leads to the formation of pulmonary edema. Novel therapies are needed to prevent or treat dysfunction of endothelial barrier.

SUMMARY OF THE INVENTION

Provided herein is an isolated peptide. The peptide may comprise KFARLWTEIPTAIT (SEQ ID NO: 1), FTEIPTI (SEQ ID NO: 3), a fragment thereof, or a variant thereof. The peptide may also consist of KFARLWTEIPTAIT (SEQ ID NO: 1), FTEIPTI (SEQ ID NO: 3), a fragment thereof, or a variant thereof. The variant may comprise a conservative substitution. The variant may comprise any peptide sequence containing Ser/Thr-x-Ile-Pro sequence, minimal EB binding consensus motif sequence. The peptide may be myristoylated or linked to a carrier peptide. The carrier peptide may be antennapedia peptide (AP). The peptide may be part of a pharmaceutical formulation, which may include a pharmaceutically acceptable excipient.

Also provided herein is a method of treating a lung injury, which may comprise administering to a patient in need thereof a composition comprising the peptide. The lung injury may be edema, inflammation-mediated vascular leakage, or asthma, which may be allergic asthma. The allergic asthma may be chronic or acute.

Also provided herein is a method of treating systemic vascular permeability syndromes, which may comprise administering to a patient in need thereof a composition comprising the peptide. The syndromes may be due to endotoxemia, trauma, or multiple transfusions. The syndromes may also be incurred as a side effect of a drug treatment, which may be systemic use of IL-2 to treat cancers.

Provided herein is a method of treating angioedema, which may comprise administering to a patient in need thereof a composition comprising the peptide. The angioedema may be allergen-induced angioedema or non-allergen-induced angioedema. The allergen-induced angioedema may be laryngeal angioedema, which may follow a food allergy or hymenopteran sting envenomation. The non-allergen-induced angioedema may be complement factor 1 inhibitor deficiency or imaging contrast dye-induced angioedema.

Also provided herein is a method of treating anaphylaxis, which may comprise administering to a patient in need thereof a composition comprising the peptide. The anaphylaxis may be allergen-induced or a non-allergic anaphylactoid reaction. The non-allergic anaphylactoid reaction may be due to a contrast dye.

Provided herein is a method of treating systemic vascular permeability, which may comprise administering to a patient in need thereof a composition comprising the peptide. The systemic vascular permeability may be associated with endotoxemia.

Also provided herein is a method of treating nasal congestion, comprising administering to a patient in need thereof a composition comprising the peptide. The nasal congestion may be associated with allergic or non-allergic rhinitis. The nasal congestion may be irritant-related or respiratory virus-related.

BRIEF DESCRIPTION OF THE DRAWINGS

FIG. 3 shows an alignment of human $IP_3$ receptors (794-814 aa of IP3R type 3) with EB binding motif (highlighted in red). The $IP_3R_3$ peptide (SEQ ID NO: 1) is shown below in green. $IP_3R_1$ isoforms 1 and 2 have SEQ ID NO: 5, $IP_3R_2$ has SEQ ID NO: 6, $IP_3R_3$ has SEQ ID NO: 7, and the EB binding motif has SEQ ID NO: 8.

DETAILED DESCRIPTION

The inventors have made the surprising discovery that peptides derived from the EB3-interacting domain of inositol 1,4,5-trisphosphate (IP3) receptor type 3 (IP$_3$R$_3$) reduce the interaction between End Binding Protein 3 (EB3) and IP$_3$R$_3$ and mitigates increased endothelial permeability response associated with cell shape changes.

Figure 21:
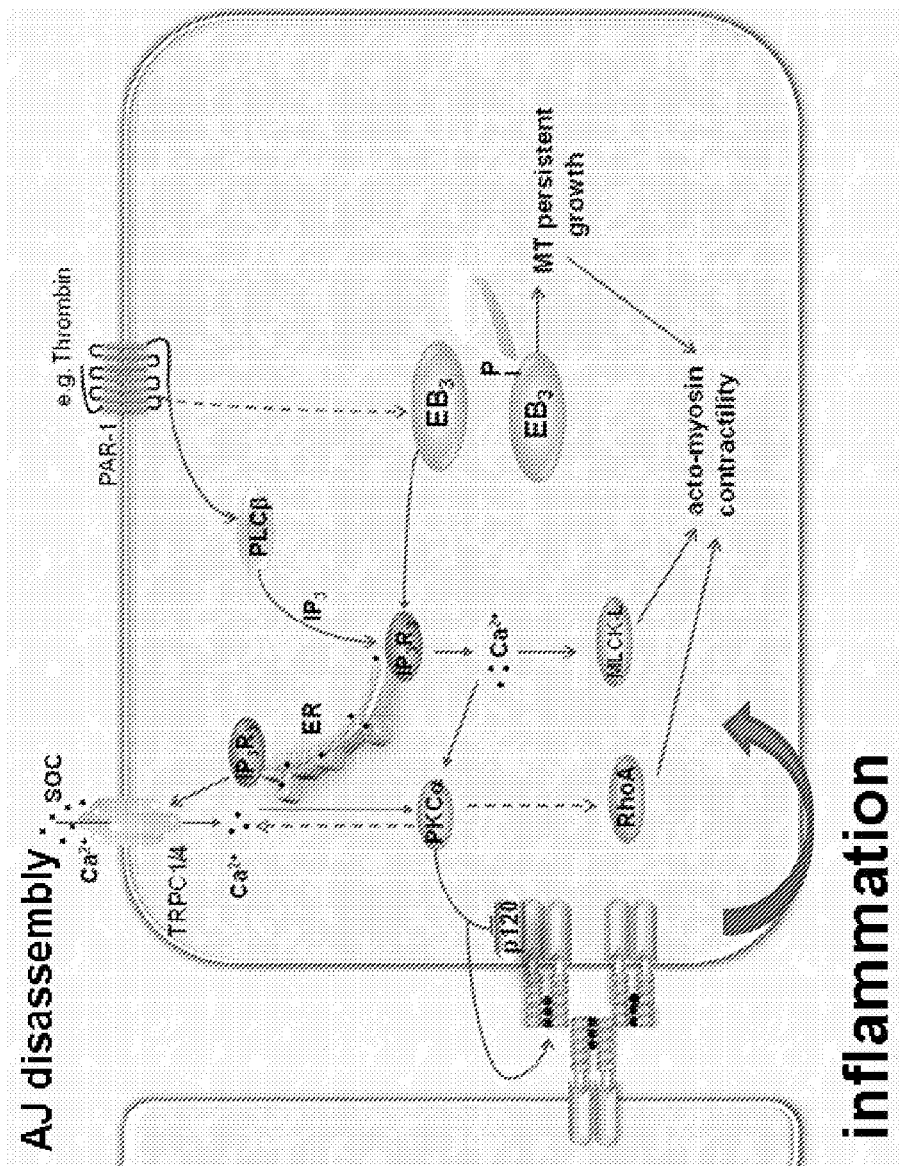
FIG. 21 shows the role of EB3 in inflammatory-induced hyper-permeability of endothelial barrier. EB3 establishes transient interactions of growing MT ends with the IP$_3$R$_3$, sensitizes the IP$_3$R$_3$ to IP$_3$ and positively regulates both Ca$^{2+}$ release from stores and SOC-dependant Ca$^{2+}$ entry during inflammation. This results in amplification of Ca$^{2+}$ signaling and increased permeability through PKCα-mediated phosphorylation of p120-catenin and acto-myosin contractility.

Based on the Examples presented below, but without being bound by theory, the role of EB3 in inflammatory-induced hyperpermeability of endothelial barrier centers on its ability to establish transient interactions of growing MT ends with IP$_3$R$_3$. As a result EB3 sensitizes IP$_3$R$_3$ to IP3 and positively regulates Ca$^{2+}$ release from the endoplasmic reticulum (ER). This leads to SOC-dependent Ca$^{2+}$ entry and amplification of Ca$^{2+}$ signaling. Increased concentration of cytosolic Ca$^{2+}$ induces PKCα-mediated phosphorylation of p120-catenin resulting in disassembly of VE-cadherin adhesions. It also facilitates RhoA-dependent acto-myosin contractility resulting in the cell shape changes. See FIG. 21.

The methods and materials described below mitigate increased endothelial permeability response associated with cell shape changes and, therefore, are useful in treating lung injury, including inflammation-mediated vascular leakage in lungs and development of edema or edema of any other organ, which may be associated with sepsis, anaphylactic reaction or acute immune response. The methods and materials may also be used to attenuate chronic vascular leak during pathological processes, such as chronic inflammation, cancer, asthma and artherogenesis.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Fragment

"Fragment" as used herein may mean a portion of a reference peptide or polypeptide or nucleic acid sequence.

b. Identical

"Identical" or "identity" as used herein in the context of two or more polypeptide or nucleotide sequences, may mean that the sequences have a specified percentage of residues or nucleotides that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

c. Peptide

A "peptide" or "polypeptide" as used herein, may refer to a linked sequence of amino acids and may be natural, synthetic, or a modification or combination of natural and synthetic.

d. Substantially Identical

"Substantially identical," as used herein may mean that a first and second protein or nucleotide sequence are at least 50%-99% identical over a region of 6-100 or more amino acids nucleotides.

e. Treat

"Treating," "treatment," or "to treat" each may mean to alleviate, suppress, repress, eliminate, prevent or slow the appearance of symptoms, clinical signs, or underlying pathology of a condition or disorder on a temporary or permanent basis. Preventing a condition or disorder involves administering a agent of the present invention to a subject prior to onset of the disease. Suppressing a condition or disorder involves administering a agent of the present invention to a subject after induction of the condition or disorder but before its clinical appearance. Repressing the condition or disorder involves administering a agent of the present invention to a subject after clinical appearance of the disease.

f. Variant

A "variant" may mean means a peptide or polypeptide that differs in amino acid sequence by the insertion, deletion, or conservative substitution of amino acids, but retain at least one biological activity. Representative examples of "biological activity" include the ability to bind to End Binding protein, a toll-like receptor (TLR) and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. Peptide

Provided herein is a peptide, which may comprise the amino acid sequence KFARLWTEIPTAIT (SEQ ID NO: 1), KFARLWAEIPTAIT (SEQ ID NO:2) (also referred to herein as IP$_3$R$_3$ Peptide), FTEIPTI (SEQ ID NO: 3) (also referred to herein as End Binding Inhibitory Peptide, or "EBIN"), a peptide disclosed in Table 3 herein, a fragment thereof, or a variant thereof. The variant may comprise a conservative substitution. The peptide may comprise an EB binding consensus motif sequence, such as the EB binding consensus sequence of IP$_3$R$_3$, or a fragment thereof. The EB binding consensus sequence of IP$_3$R$_3$ may be Ser/Thr-x-Ile-Pro. The peptide may consist of KFARLWTEIPTAIT (SEQ ID NO: 1), KFARLWAEIPTAIT (SEQ ID NO:2), FTEIPTI (SEQ ID NO: 3), a consensus sequence comprising Ser/Thr-x-Ile-Pro, a peptide disclosed in Table 3 herein, a fragment of the foregoing, or a conservative variant of the foregoing. The variant may comprise any peptide sequence containing Ser/Thr-x-Ile-Pro sequence, minimal EB binding consensus motif sequence.

The peptide may be conjugated, myristoylated or linked to another peptide, such as a carrier peptide. The peptide may be an antennapedia peptide.

3. Methods of Treatment

Provided herein is a method of treating lung injury. The lung injury may be lung inflammation, which may be inflammation-mediated vascular leakage and/or the development of edema. The lung injury may be an acute lung injury. The lung injury may also be chronic vascular leak such as observed in patients with asthma. The treatment may attenuate the chronic vascular leak. The lung injury may be hyperpermeability of vessels in the lung, including systemic vascular permeability, such as in endotoxemia. The lung injury may be associated with sepsis, inflammation, severe multiple trauma, aspiration of saliva/gastric contents, aspiration pneumonia, shock, near-drowning, multiple transfusions, inhalation of irritants or toxic fumes, artherogenesis, mechanical injury (ventilation-induced injury) or radiation exposure. Also provided herein is a method of treating asthma and/or improving lung function and overall health of patients with asthma. The asthma may be allergic asthma, which may be chronic or acute.

Also provided herein is a method of treating anaphylaxis, such as allergen-induced anaphylaxis, and non-allergic anaphylactoid reactions, such as to contrast dyes. Further provided herein is a method of treating angioedema, including allergen-induced angioedema, such as laryngeal edema, which may follow food allergy or hymenopteran sting envenomation. The angioedema may also be non-allergen-induced angioedema, such as in complement factor 1 inhibitor deficiency or imaging contrast dye-induced anaphylactoid reactions.

Provided herein is a method of treating systemic vascular permeability syndromes. The syndromes may be due to endotoxemia, trauma, or multiple transfusions. The syndromes may also be incurred as a side effect of a drug treatment. The drug treatment may be systemic use of IL-2 to treat cancers. Also provided is a method of treating nasal congestion. The congestion may be associated with allergic or non-allergic rhinitis. The congestion may be irritant-related or respiratory virus-related.

The method may comprise administering to the mammal a composition comprising a therapeutically effective amount of the peptide. The composition may be a pharmaceutical formulation. The composition comprising the peptide may be administered in combination with one or more other peptides, compounds, and/or pharmaceutical compositions useful for treating lung injury. The one or more other peptides, compounds, and/or pharmaceutical compositions may be any agent that treats the lung injury including, but not limited to preload reducers such as nitroglycerin and diuretics, such as furosemide (Lasix). Such medications dilate the veins in the lungs and elsewhere in the body, which decreases fluid pressure going into the heart and lungs. Other one or more compounds include afterload reducers. These drugs dilate the peripheral vessels and take a pressure load off the left ventricle. Some examples of afterload reducer medications include nitroprusside (Nitropress), enalapril (Vasotec) and captopril (Capoten).

a. Subject

The subject may be a mammal, which may be a human. Prior to diagnosis, the subject may be at risk for lung injury because of exposure to one or more risk factors, heart condition, etc. The one or more risk factors may include, for example, the subject having a family history of cancer, age, smoking tobacco, drinking alcoholic beverages, and/or dietary deficiency. The subject may be exposed to toxic fumes or radiation, mechanical ventilation. The subject may have burn wounds, inflammation, severe multiple trauma, aspiration of saliva/gastric contents, aspiration pneumonia, sepsis, shock, near-drowning, multiple transfusions.

b. Administration

Administration of the peptides using the method described herein may be systemically, orally, parenterally, sublingually, transdermally, rectally, transmucosally, topically, via inhalation, via buccal administration, nasally, or combinations thereof. Parenteral administration includes, but is not limited to, intravenous, intraarterial, intraperitoneal, subcutaneous, intramuscular, intrathecal, and intraarticular. Administration may also be subcutaneous, intravenous, via intra-air duct, or intra-tumoral. For veterinary use, the peptide may be administered as a suitably acceptable formulation in accordance with normal veterinary practice. The veterinarian can readily determine the dosing regimen and route of administration that is most appropriate for a particular animal. The peptides may be administered to a human patient, cat, dog, large animal, or an avian.

The peptide may be administered as a monotherapy or simultaneously or metronomically with other treatments, which may be a surgery or removal of a tumor. The term "simultaneous" or "simultaneously" as used herein, means that the peptide and other treatment be administered within 48 hours, preferably 24 hours, more preferably 12 hours, yet more preferably 6 hours, and most preferably 3 hours or less, of each other. The term "metronomically" as used herein means the administration of the peptide at times different from the other treatment and at a certain frequency relative to repeat administration.

The peptide may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The peptide may be administered at any point prior to a second treatment of the peptide including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins., 2 mins, and 1 mins.

The peptide may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The peptide may be administered at any point prior after a second treatment of the peptide including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

c. Formulation

The method may comprise administering the peptide. Peptides provided herein may be in the form of tablets or lozenges formulated in a conventional manner. For example, tablets and capsules for oral administration may contain conventional excipients may be binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers may be lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants may be potato starch and sodium starch glycollate. Wetting agents may be sodium lauryl sulfate. Tablets may be coated according to methods well known in the art.

Peptides provided herein may also be liquid formulations such as aqueous or oily suspensions, solutions, emulsions, syrups, and elixirs. The peptides may also be formulated as a dry product for constitution with water or other suitable vehicle before use. Such liquid preparations may contain additives such as suspending agents, emulsifying agents, nonaqueous vehicles and preservatives. Suspending agent may be sorbitol syrup, methyl cellulose, glucose/sugar syrup, gelatin, hydroxyethylcellulose, carboxymethyl cellulose, aluminum stearate gel, and hydrogenated edible fats. Emulsifying agents may be lecithin, sorbitan monooleate, and acacia. Nonaqueous vehicles may be edible oils, almond oil, fractionated coconut oil, oily esters, propylene glycol, and ethyl alcohol. Preservatives may be methyl or propyl p-hydroxybenzoate and sorbic acid.

Peptides provided herein may also be formulated as suppositories, which may contain suppository bases such as cocoa butter or glycerides. Peptides provided herein may also be formulated for inhalation, which may be in a form such as a solution, suspension, or emulsion that may be administered as a dry powder or in the form of an aerosol using a propellant, such as dichlorodifluoromethane or trichlorofluoromethane. Peptides provided herein may also be formulated as transdermal formulations comprising aqueous or nonaqueous vehicles such as creams, ointments, lotions, pastes, medicated plaster, patch, or membrane.

Peptides provided herein may also be formulated for parenteral administration such as by injection, intratumor injection or continuous infusion. Formulations for injection may be in the form of suspensions, solutions, or emulsions in oily or aqueous vehicles, and may contain formulation agents including, but not limited to, suspending, stabilizing, and dispersing agents. The peptide may also be provided in a powder form for reconstitution with a suitable vehicle including, but not limited to, sterile, pyrogen-free water.

Peptides provided herein may also be formulated as a depot preparation, which may be administered by implantation or by intramuscular injection. The peptides may be formulated with suitable polymeric or hydrophobic materials (as an emulsion in an acceptable oil, for example), ion exchange resins, or as sparingly soluble derivatives (as a sparingly soluble salt, for example).

d. Dosage

The method may comprise administering a therapeutically effective amount of the peptide to a patient in need thereof. The therapeutically effective amount required for use in therapy varies with the nature of the condition being treated, the length of time desired to activate TLR activity, and the age/condition of the patient. In general, however, doses employed for adult human treatment typically are in the range of 0.001 mg/kg to about 200 mg/kg per day. The dose may be about 0.05 mg/kg to about 10 g/kg per day. The desired dose may be conveniently administered in a single dose, or as multiple doses administered at appropriate intervals, for example as two, three, four or more sub-doses per day. Multiple doses may be desired, or required.

The dosage may be at any dosage such as about 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 25 mg/kg, 50 mg/kg, 75 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg, 1 g/kg, 2 g/kg, 3 g/kg, 4 g/kg, 5 g/kg, 6 g/kg, 7 g/kg, 8 g/kg, 9 g/kg, or 10 g/kg.

4. Kit

Provided herein is a kit, which may be used for treating a lung injury. The kit may comprise one or more of the peptides. The peptides may be part of a pharmaceutical composition. The kit may further comprise instructions for using the kit and conducting the administering the peptide or formulation.

The kit may also comprise one or more containers, such as vials or bottles, with each container containing a separate reagent. The kit may further comprise written instructions, which may describe how to perform or interpret the method described herein.

The present invention has multiple aspects, illustrated by the following non-limiting examples.

EXAMPLES

Example 1

Depletion of EB3 Inhibits Release of Ca2+ from Stores

Figure 1:
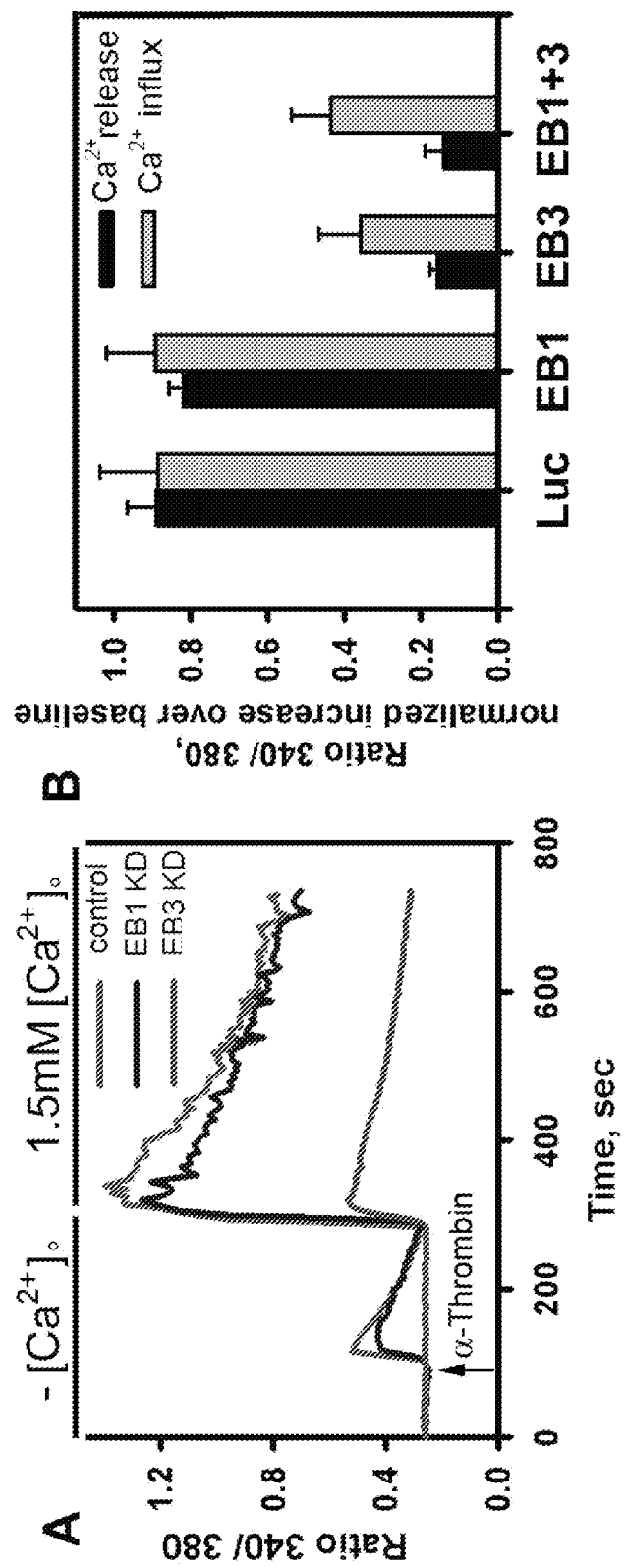
FIG. 1 shows the depletion of EB3 inhibits $Ca^{2+}$ release from stores in response to activation of Protease-activated receptor (PAR)-1. A. HMVECs expressing either shRNA to EB1, EB3 and Luciferase were loaded with Fura 2-AM and 340 ($Ca^{2+}$-bound) Fura/380 (Free Fura) ratio was calculated after stimulation of cells with thrombin (50 nM) in the absence ($-[Ca^{2+}]_o$) and in the presence (1.5 mM $[Ca^{2+}]_o$) of extracellular $Ca^{2+}$. Arrow, time of thrombin addition. Note that deletion of EB3 markedly reduced the increase in intracellular $Ca^{2+}$ concentration. B. Plot shows the mean±SD for thrombin-induced $Ca^{2+}$ release and entry calculated as a maximum increase over the basal value. The increase is normalized to control non-transfected cells from the same coverslip (n=9).

Previous work suggested the role of the MT cytoskeleton in regulating IP3-gated release of $Ca^{2+}$ from ER stores. The ability of EB3 to regulate release of $Ca^{2+}$ from IP3-sensitive stores downstream of PAR-1 signaling was tested. It was determined that the changes in intracellular $Ca^{2+}$ concentration in HMECs expressing shRNA to EB1, EB3 and Luciferase in response to PAR-1 activation (FIG. 1). Because our vector-based siRNA constructs were cloned into a GFP-C1 vector, we were able to compare the changes in non-transfected and transfected cell from the same coverslip. Depletion of EB1 did not have any effect on the release of $Ca^{2+}$ from stores as compared to control non-transfected cells or cells expressing shRNA to Luciferase. In contrast, depletion of EB3 led to marked inhibition of $Ca^{2+}$ release, thus resulting in decreased $Ca^{2+}$ influx. The effect of simultaneous depletion of EB1 and EB3 was comparable with depletion of EB3 alone (FIG. 1 B). These data suggest that EB3 is requires for ER $Ca^{2+}$ depletion.

Example 2

Role of EB3 Interaction with IP3R in the Mechanism of IP3-Gated Release of Ca2+

Figure 2:
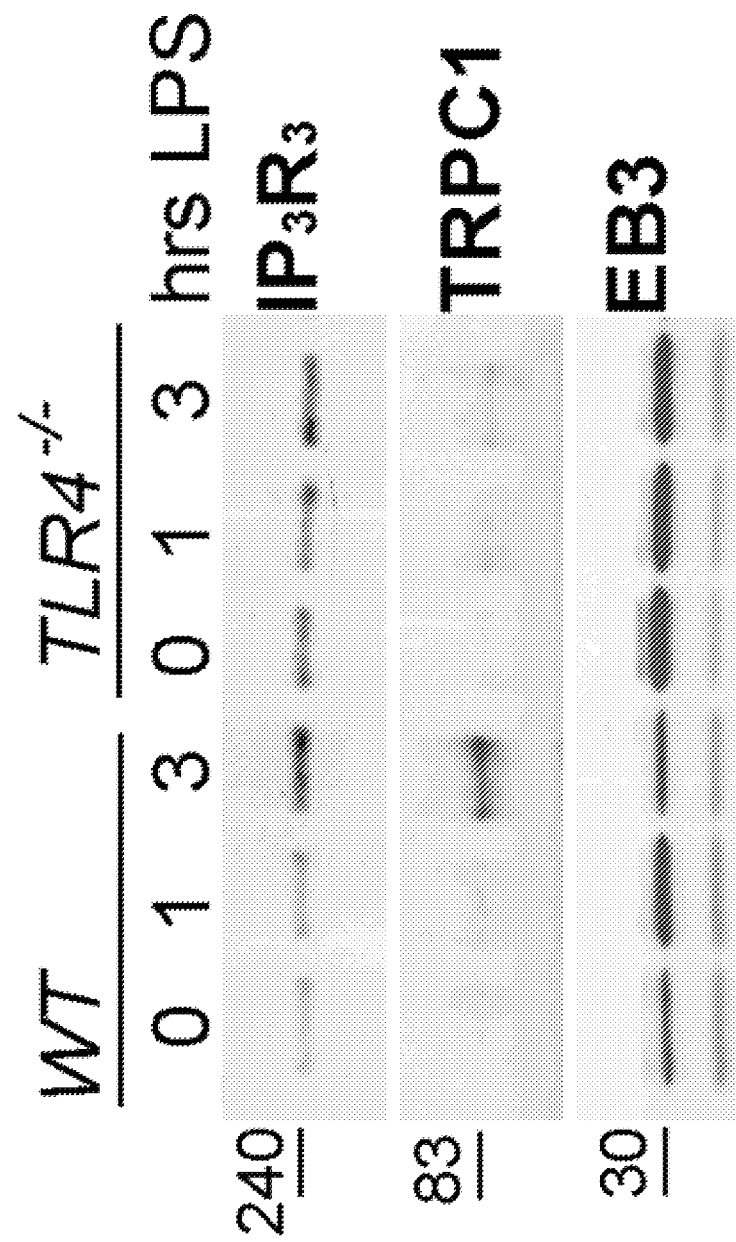
FIG. 2 shows EB3 interaction with IP3R3 and TRPC1 in the context of lung inflammation. WT and TLR4 KO mice received single intraperitoneal injection (i.p.) of endotoxin Lipopolysaccharides (LPS), the component of the outer membrane of Gram-negative bacteria, which elicits strong immune response in mammals, at 10 mg/kg body weight. Lungs were isolated at indicated times. EB3 was IP'ed from whole lung homogenates. Resulting precipitates were probed for TRPC1, $IP_3R_3$ and EB3. Note, deletion of TLR4 (LPS receptor) alters EB3 interaction with TRPC1. It is also prevents increase in binding to $IP_3R_3$. Note, EB3 binding to $IP_3R_3$ in TLR4$^{-/-}$ lungs is comparable to WT. Data is representative of 2 independent experiments.

It was determined whether EB3 interacts with $IP_3R$ type 3, activity of which is critical for the thrombin-induced release of $Ca^{2+}$ in ECs. Mice were challenged with sub-lethal dose of LPS and determined the association of EB3 with $IP_3R_3$ and TRPC1 (SOC) channel. As shown on FIG. 2, EB3 interacts with $IP_3R_3$ in resting endothelial microvasculature and the level of this interaction increases during LPS-induced lung inflammation. Interestingly, TRPC1 was also found in the EB3 precipitated in the lungs undergoing inflammation (3 hrs of LPS challenge). These changes were not observed in TLR4 (LPS receptor) KO mice indicating for causal relationship of these interactions and inflammation.

Figure 4:
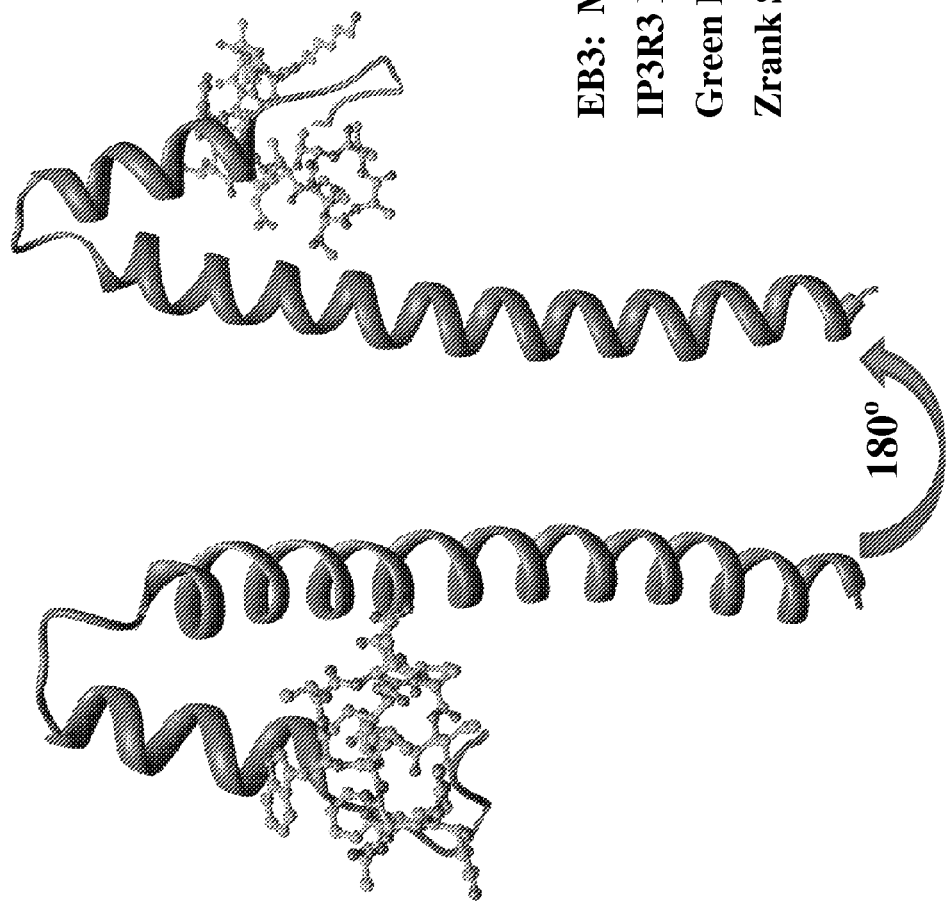
FIG. 4 shows a ribbon representation of EB3 structure (magenta) and IP3R3 derived peptide (SEQ ID NO: 1) (Green ball and stick) docked into EB3 hydrophobic binding groove of EB3; 180° rotation is shown. The IP3R3 derivative peptide was docked using a Z-Dock program in conjunction with Discovery Studio 3.0 software. The binding energy between the peptide and EB3 was calculated to be −68.882 kcal/mol.
Figure 5:
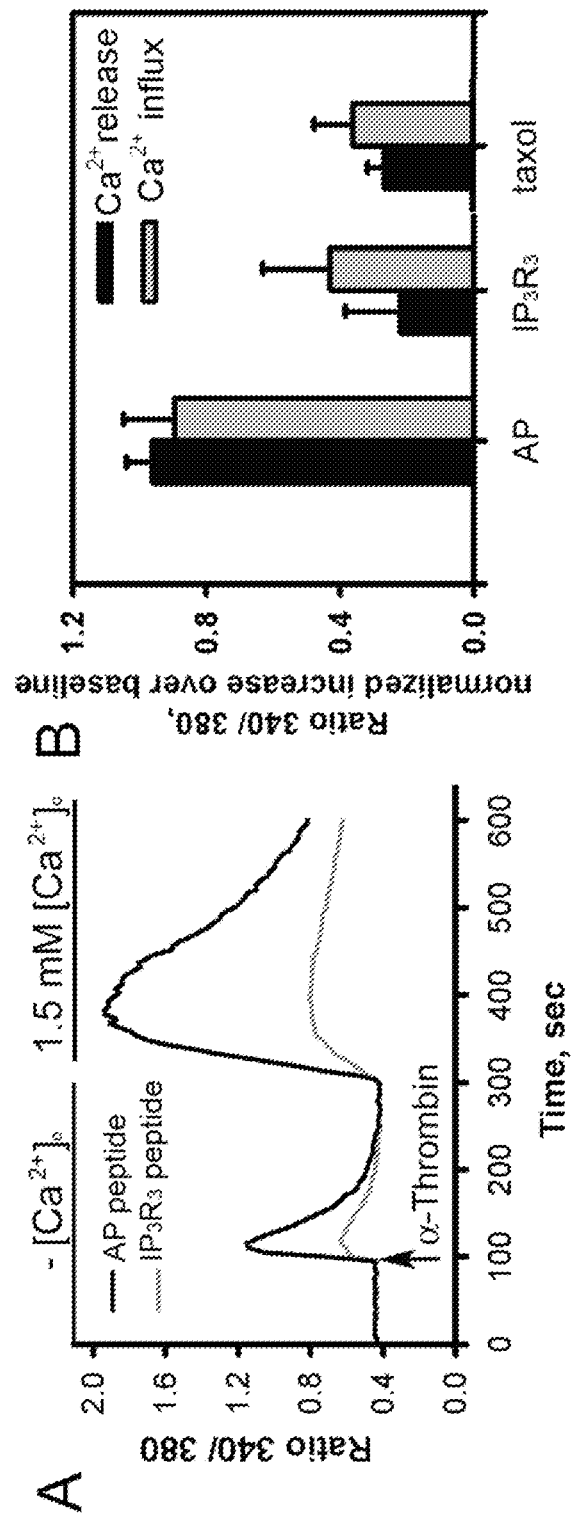
FIG. 5 shows $IP_3R_3$ peptide (SEQ ID NO: 1) inhibits $Ca^{2+}$ release from ER in response to PAR-1 activation. A. HMVECs pre-treated with AP-attached $IP_3R_3$ peptide or control (AP) peptide were loaded with Fura 2-AM and 340/380 ratio was calculated after stimulation of cells with thrombin (50 nM) in the absence and in the presence of extracellular $Ca^{2+}$. Arrow, time of thrombin addition. B. Plot shows the mean±SD for thrombin-induced $Ca^{2+}$ release and entry calculated as a maximum increase over the basal value. The increase is normalized to control non-treated cells from the same experiment (n=4).

Interestingly, $IP_3R_3$ contains EB binding consensus motif, Ser/Thr-x-Ile-Pro (SxIP). A short peptide based on $IP_3R_3$ sequence (KFARLWTEIPTAIT—SEQ ID NO: 1) (FIG. 3) shows high binding activity for EB3 with free energy binding of −68.882 kcal/mol (FIG. 4). The pre-treatment of cell with $IP_3R_3$ sequence attached to the C-terminus of cell permeant antennapedia peptide (AP) at 10 nM markedly decreased the release of Ca2+ from stores in response to thrombin (FIG. 5A), suggesting that interaction between $IP_3R_3$ and EB3 is critical in the mechanism of $IP_3R$ activation. The effects of $IP_3R$ peptide and taxol were compared in regulating $Ca^{2+}$ release. It was found that pre-treatment of cells with 5 µg/ml taxol for 20 min prior to thrombin stimulation inhibits release of $Ca^{2+}$ from ER to the same extent as $IP_3R_3$ peptide (FIG. 5 B).

Example 3

Figure 6:
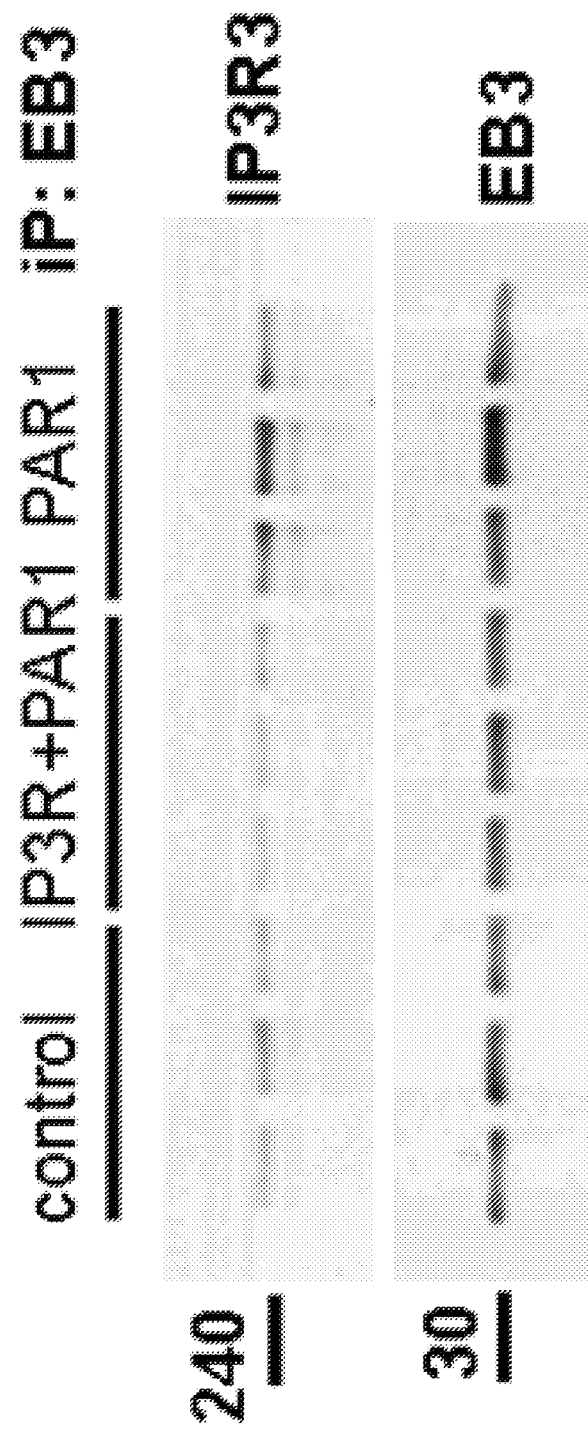
FIG. 6 shows $IP_3R_3$ peptide (SEQ ID NO: 1) inhibits interaction between EB3 and $IP_3R_3$ in ex vivo lung preparations. Isolated lungs underwent a 20-min equilibration perfusion followed by 30 min of perfusion with 10 μM AP-$IP_3R_3$ peptide. At 5 min thereafter, 30 μM PAR-1 agonist peptide TFLLRN-NH2 (PAR-1 a.p.) was infused for 20 min (group $IP_3R_3$+PAR-1). Another group was infused only with the 30 μM PAR-1 agonist peptide (group PAR-1). Lungs were used thereafter to prepare lung homogenate which was used to determine the effect of $IP_3R_3$ peptide on EB3/$IP_3R_3$ interaction. EB3 was immunoprecipitated with specific antibody and resulting precipitates were probed for EB3 and $IP_3R_3$. Note, activation of PAR-1 receptor significantly increases EB3/$IP_3R_3$ interaction (group PAR-1) as compared to basal level (control group) whereas profusion of $IP_3R_3$ peptide inhibits this interaction in activated lung microvasculature.
Figure 7:
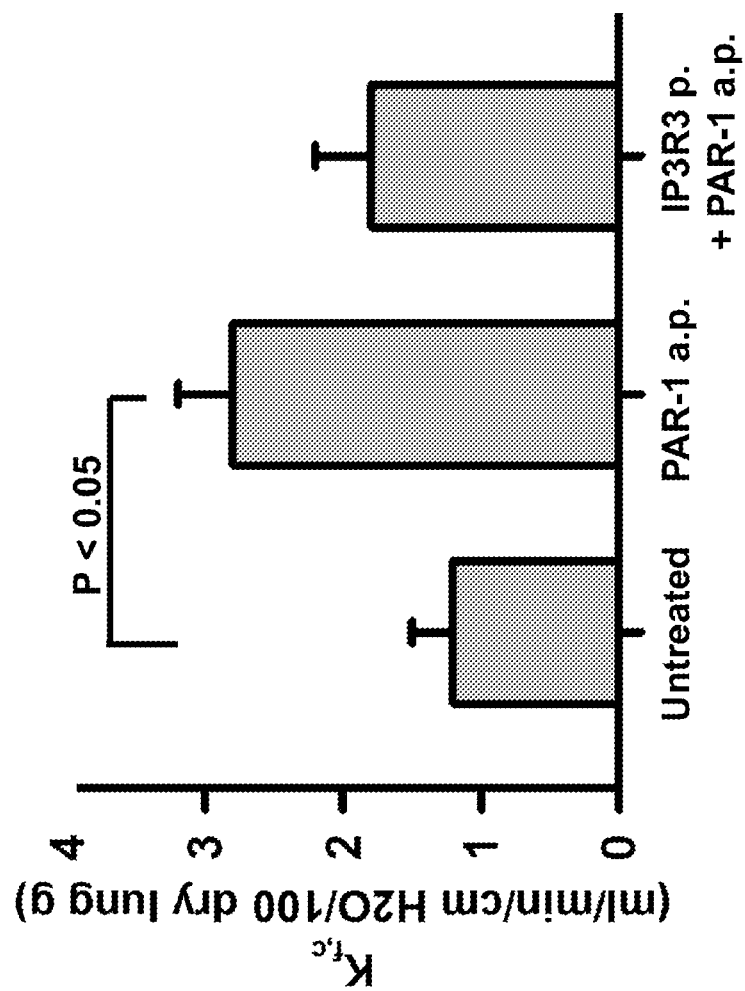
FIG. 7 shows $IP_3R_3$ peptide (SEQ ID NO: 1) mitigates the increase in lung vascular permeability ($K_{f,c}$, microvascular filtration coefficient) in response to PAR-1 activation. Ex vivo lung preparations underwent a 20-min equilibration perfusion followed by 30 min of perfusion with 10 μM AP-$IP_3R_3$ peptide. At 5 min thereafter, 30 μM PAR-1 agonist peptide TFLLRN-NH2 (PAR-1 a.p.) was infused for 20 min prior to $K_{f,c}$ measurement. n=3-5 per group. Bars±SD *p<0.05 by ANOVA. Note, there is no significant change in vascular permeability in response to PAR-1 activation in lungs profused with AP-$IP_3R_3$.

$IP_3R_3$ Peptide Prevents Inflammation-Induced Pulmonary Vascular Leakage and Lethality in Sepsis To address the role of EB3/IP3R interaction in regulating vascular endothelial permeability we used ex vivo lung preparations. The peptide was infused into lungs for 30 minutes prior to infusion of PAR-1 agonist peptide and the interaction between EB3 and $IP_3R_3$ was determined by IP assay (FIG. 6). Activation of PAR-1 receptor significantly increased the EB3/$IP_3R_3$ interaction as compared to basal level whereas profusion of $IP_3R_3$ peptide inhibited this interaction in activated lung microvasculature. Consequently, $IP_3R_3$ peptide mitigated the increase in lung vessel permeability as measured by changes in microvascular filtration coefficient, Kf,c. FIG. 7 demonstrates that $IP_3R_3$ peptide markedly attenuates the increase in microvascular permeability in response to PAR-1 activation. These data suggest that interaction between EB3 and IP3R might be important for inflammation-induced vascular leakage and development of edema in lungs.

Figure 8:
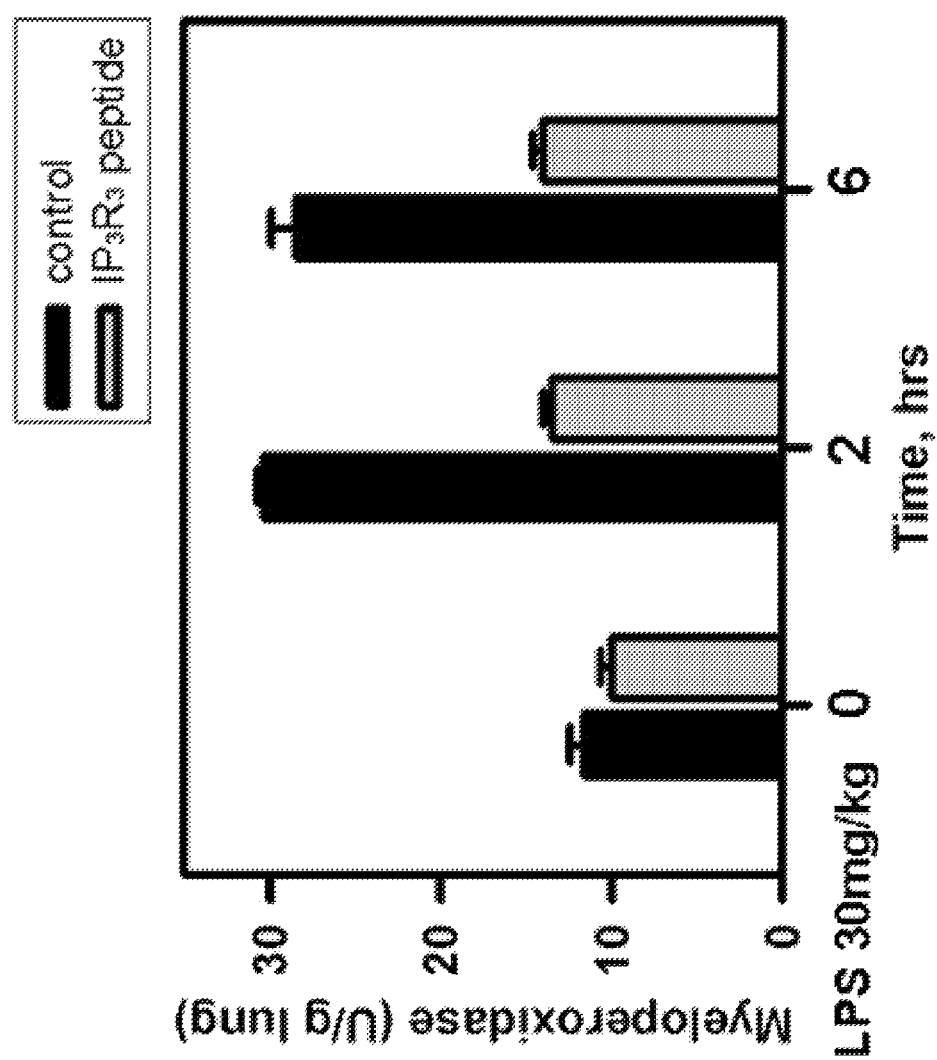
FIG. 8 shows $IP_3R_3$ peptide (SEQ ID NO: 1) mitigates infiltration of neutrophils in lung in the context of LPS-induced inflammation. Mice received a single i.p. injection of LPS (30 mg/kg body weight; E. Coli LPS 0111:B4; LD50 dose) and were used for analysis at 2 and 6 hrs. Lungs were perfused with PBS, weighed, frozen and used for measuring lung myeloperoxidase (MPO) activity, a measure of pulmonary neutrophils (PMN) in lungs. n=6 mice/group.
Figure 9:
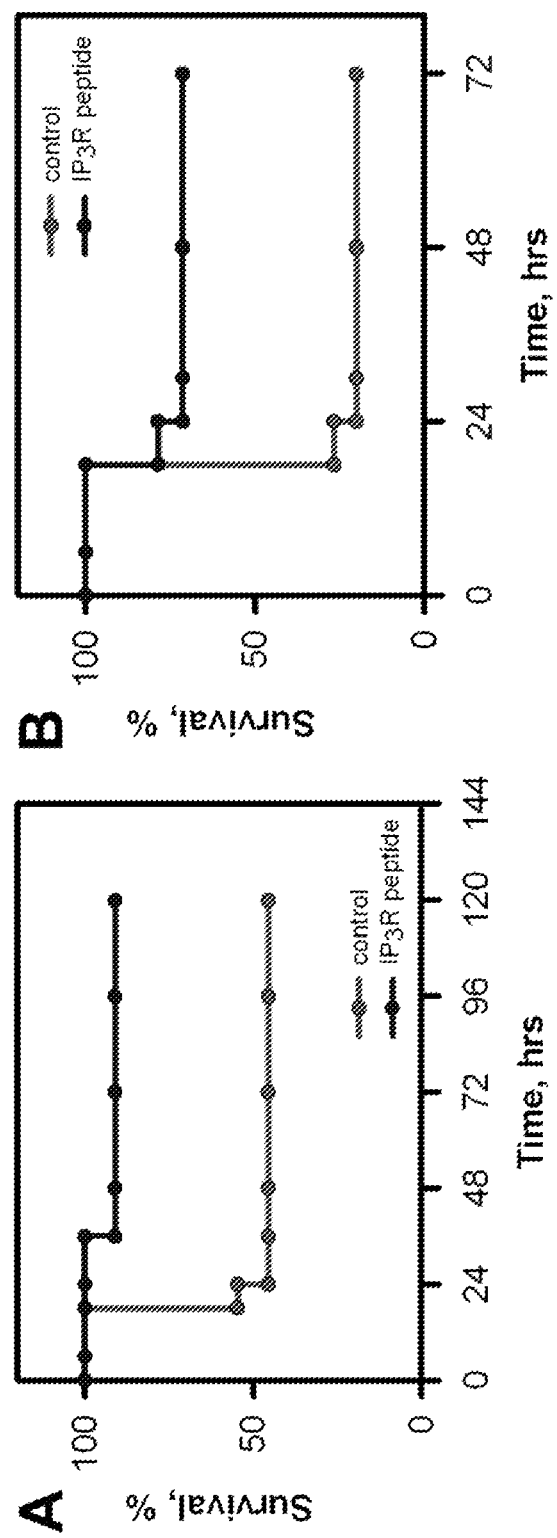
FIG. 9 shows $IP_3R_3$ peptide (SEQ ID NO: 1) prevents lethality in LPS-induced sepsis. Mice treated with $IP_3R_3$ peptide prior to LPS injection demonstrated mortality reduction in LD50- (30 mg/kg LPS, A) and LD90-challenged (50 mg/kg LPS, B) control mice. (n=11-15 mice/group, p<0.001 AP-$IP_3R_3$ vs control treatment (AP control) by ANOVA. Mice were anesthetized prior to retro-orbital i.v. injection of $IP_3R_3$ with a mixture of ketamine, 10 mg/ml; xylazine, 0.25 mg/ml and acepromazine, 0.25 mg/ml.
Figure 10:
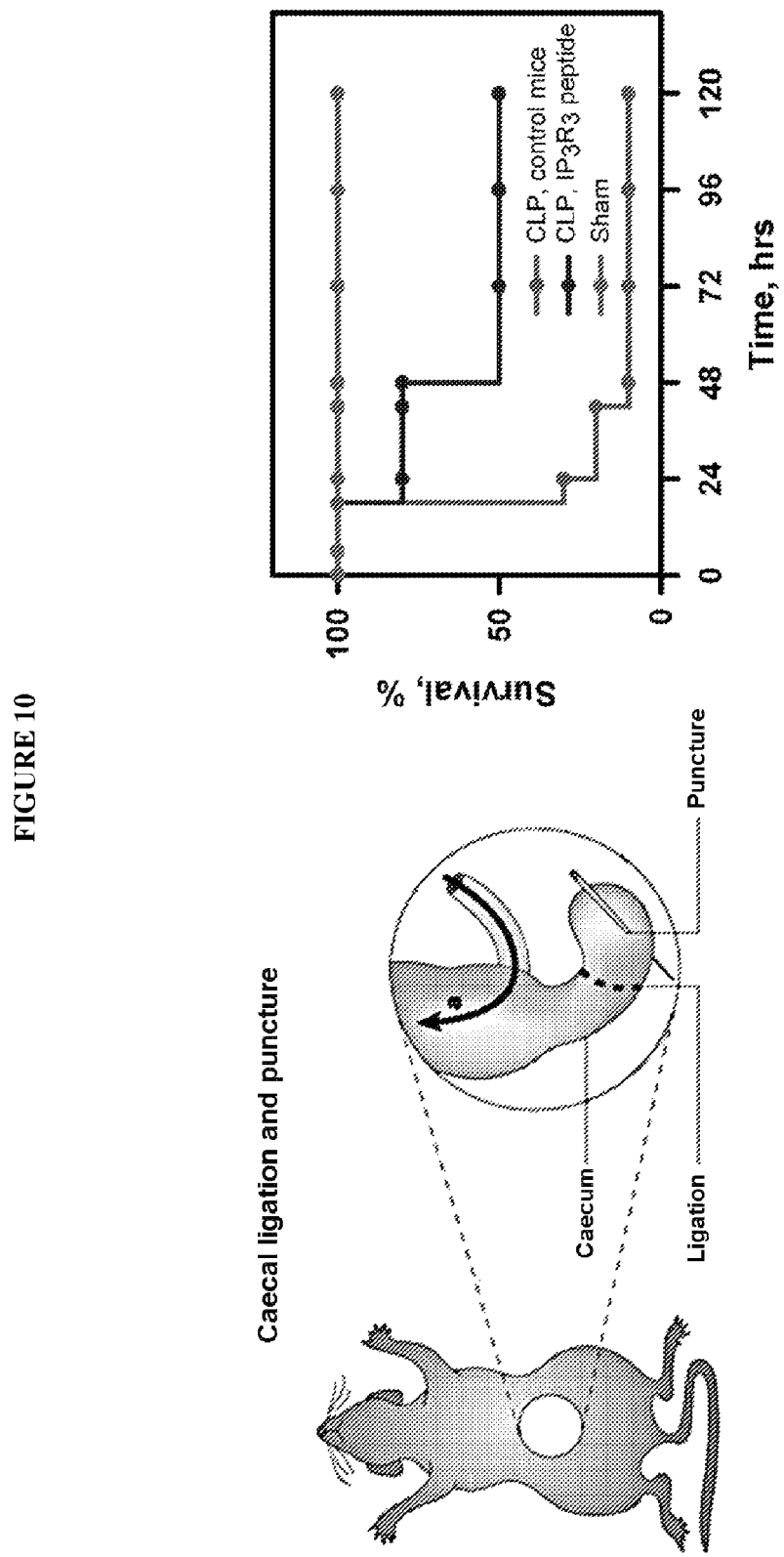
FIG. 10 shows that $IP_3R_3$ peptide (SEQ ID NO: 1) prevents lethality in polymicrobial sepsis. Mice treated with $IP_3R_3$ peptide experience reduced mortality in the 120-hr period after CLP. 6-8 week-old CD-1 mice were i.v. injected with $IP_3R_3$ peptide (1 μM/kg body weight) 30 min prior to and 24 and 48 hrs after CLP surgery. The cecum was ligated at its midpoint and the cecal contents were gently pushed towards the distal part. The cecum was punctured midway between the ligation and the tip of the cecum in a mesentric-to-anti-mesentric direction using a 16-gauge needle. A small amount of feces was extruded from both the mesentric and anti-mesentric penetration holes. In sham controls, only laparotomy was performed. Mice were anesthetized. Survival was significantly higher in IP$_3$R$_3$ peptide group than the control (n=10 mice/group). Difference in mortality was assessed by log-rank test (p<0.05).

Recent studies demonstrated that vascular leakage is a critical factor contributing to lethality in sepsis. The pharmacological effect of $IP_3R_3$ peptide was tested in LPS-induced murine model of sepsis. Male CD1 mice were challenged by intraperitoneal injection (i.p.) of LPS (30 mg/kg body weight) and infiltration of neutrophils in lung, a measure of lung inflammation was determined. Lungs were perfused with PBS, weighed, frozen and used for measuring lung myeloperoxidase (MPO) activity, signature of activated neutrophils. As shown in FIG. 8, treatment of mice with $IP_3R_3$ peptide 30 minutes prior to LPS challenge, significantly reduced infiltration of neutrophils in lung at 2 and 6 hrs of LPS challenge as compared to control peptide treated group. This observation suggests that $IP_3R_3$ peptide attenuated LPS-induced lung inflammation and injury. Consequently, mice received a treatment of $IP_3R_3$ peptide, 30 minutes prior to and 1 hr after LPS administration, demonstrated marked improvement in survival rate of control groups in both, LD50- and LD80-challenge (FIG. 9). Furthermore, it was determined whether $IP_3R_3$ peptide protects from polymicrobial sepsis induced by cecal ligation and puncture (CLP). CLP causes lethal peritonitis that is accompanied by acute lung injury (ALI). It is well-excepted and clinically relevant method in experimental rodents. FIG. 10 shows that $IP_3R_3$ peptide improved survival of animal after CLP. Whereas 90% control mice died within the first 48 hrs, animals injected with $IP_3R_3$ before surgery and 24 and 48 hrs after surgery, demonstrated significantly higher survival rate.

Figure 11:
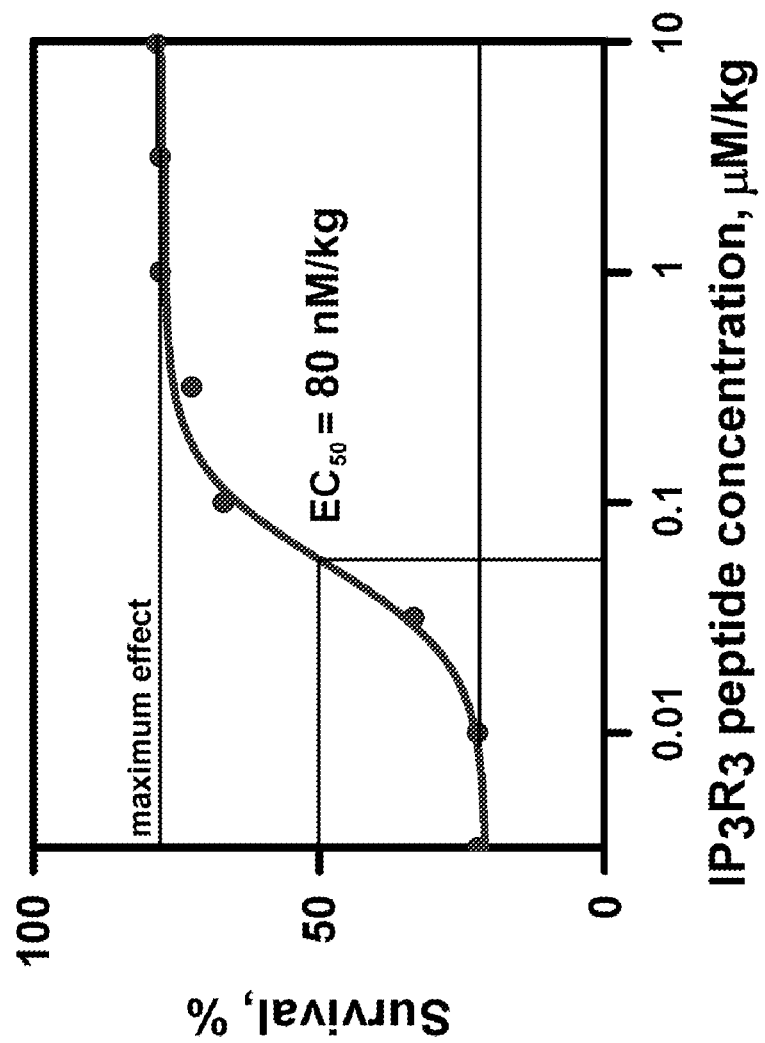
FIG. 11 shows IP$_3$R$_3$ peptide dose-response on mice survival. CD-1 mice treated with indicated doses of IP$_3$R$_3$ peptide were i.p. injected with LPS at LD80 dose (50 mg/kg LPS) and were monitored for 5 days. Survival rate (%) was plotted vs. peptide dose in logarithm scale. The sigmoidal dose-response curve was fitted to the data points. n=10 mice/group. Mice were anesthetized prior to retro-orbital injection of peptide with 2.5% isoflurane in room air in an anesthesia induction chamber. Anesthesia was maintained during i.v. injection using a specially designed rodent facemask with a coaxial tube (Harvard Apparatus, AH 72-3026).

These data suggest that $IP_3R_3$ peptide derivative peptide can be potentially used for preventing pulmonary hyper-permeability and for attenuating chronic vascular leak during pathological processes such as inflammation and artherogenesis. The dose-response of $IP_3R_3$ peptide was further tested in LPS-induced murine model of sepsis. Male CD1 mice were challenged by i.p. injection of LPS at LD80 dose. Mice received a retro-orbital i.v. injection of $IP_3R_3$ peptide at doses 0.01, 0.033, 0.1, 0.33, 1.0, 3.3 and 10 µM per kg of the body weight. Mice were injected with $IP_3R_3$ peptide three times, 30 minutes prior to, and 1 and 24 hrs after LPS administration. A percent of survived animals in each group was plotted as a function of $IP_3R_3$ dose. FIG. 11 shows that $IP_3R_3$ peptide improved survival rate of control groups starting at 0.033 µM/kg and reached a maximal efficacy at 1 µM/kg. Increase in $IP_3R_3$ dose did not lead to further improvement but importantly, neither it caused animal death. These data suggest that $IP_3R_3$ peptide has low toxicity within this range of doses. The $ED_{50}$ (effective dose, 50%) as 80 nM/kg was calculated using a three-parameter logistic equation:

$$y=\min+(\max+\min)/1+10^{LogED50-x}$$

Where min and max are minimum and maximum of response. The presented data suggest that $IP_3R_3$ is a potential drug with a high potency and low toxicity. In contrast to taxol, this drug is not expected to display a general toxicity.

EB3 positively regulates release of $Ca^{2+}$ from ER stores, and thereby increases endothelial barrier permeability in response to pro-inflammatory stimuli. The interaction between EB3 and $IP_3R$ is important in the mechanism of IP3-gated release of $Ca^{2+}$ $IP_3R_3$ peptide prevents inflammation-mediated vascular leakage in lungs and development of edema and markedly improves the survival of mice in two different models of sepsis.

Example 4

To Determine the Role of EB3 Regulation of Ca2+ Signaling in the Mechanism of Increased Endothelial Permeability and Lung Edema Formation We postulate that dynamic interaction of EB3 at the MT ends with ER is required for propagation of $Ca^{2+}$ waves and increased endothelial barrier permeability in response to pro-inflammatory mediators.

Hypothesis: EB3 regulation of IP3-gated release of $Ca^{2+}$ from ER is required for the MT-dependent increase in endothelial permeability. We will address the idea that accumulation of EB3 at the growing MT ends facilitates transient interaction of EB3 with IP3R and positively regulates release of $Ca^{2+}$ from stores thus resulting in SOC-dependent $Ca^{2+}$ entry, activation of $Ca^{2+}$-dependent PKCα isoform, PKCα-mediated phosphorylation of p120-catenin and VE-cadherin internalization (as postulated by model in FIG. 21).

Example 5

Role of EB3 in Regulating Persistent MT Growth and IP3R Activation

MT-destabilizing and stabilizing agents inhibit IP3-induced Ca2+ release 11-13. Our Preliminary Data demonstrate that depletion of EB3 but not EB1 in endothelial cells also inhibits PAR-1 mediated release of Ca2+ from stores. We will determine whether EB3 regulates IP3-induced Ca2+ release from ER indirectly through regulation of MT dynamics. We will determine whether restoration of MT persistent growth in EB3 depleted cells by expressing the artificial EB3 dimer as shown by us 20 can also restore PAR-1 mediated release of Ca2+ from ER. Since artificial dimer EB3-NL-LZ is completely devoid of any domain responsible for the binding to known EB partners, it is not expected to restore IP3-induced Ca2+ release if interaction between EB3 and IP3R is critical for activation of IP3R. Therefore, if we will observe a restoration of IP3R activity in cells expressing the artificial EB3 dimers, we will conclude that EB3 regulates agonist-induced Ca2+ release from ER indirectly, via MT dynamics. This experiment will address thrombin-mediated release of Ca2+ from ER and influx of extracellular Ca2+ as assessed by 340/380 ratiometric imaging of Fura2-AM in HMLVECs. Based on the validity of our hypothesis, we predict that expression of EB3-NL-LZ will not restore the agonist-induced release of Ca2+ from ER.

Example 6

Role of EB3 Interaction with IP3R in the Intracellular Distribution of IP3R

On the premises of our Data we proposed that interaction between EB3 and IP3R type 3 might be important in the mechanism of receptor activation. IP3R contains the Ser/Thr-x-Ile-Pro (SxIP) consensus motif (FIG. 17), which is a specific signature of EB-interacting partners. The phosphorylation of Ser or Thr in the vicinity of this motif markedly decreases the affinity of EB1 for its known partners. We will determine whether the short IP3R sequence peptide (798-811; KFARLWTEIPTAIT—SEQ ID NO: 1) fused with AP sequence disrupts the interaction between IP3R and EB3 and whether it inhibits thrombin-induced IP3-gated release of Ca2+. Because there is some possibility that the peptide can be phosphorylated in cells, we will express Avi-tagged IP3R peptide and will determine its phosphorylation by autoradiography. If we find that peptide undergoes phosphorylation, we will use phosphorylation-defective peptide in which first Thr will be substituted for Ala (phosphorylation defective peptide; KFARLWAEIPTAIT—SEQ ID NO:2) as more potent for all other studies. The binding of the peptide to EB3 will be confirmed in cells and in vitro by co-IP and pull-down assay. We will use this peptide to disrupt the interaction between EB3 and IP3R in cells. It is our expectation that IP3R peptide will inhibit Ca2+ release from stores in response to thrombin.

We will investigate whether EB3 depletion or inhibition of interaction between EB3 and IP3R with blocking peptide changes the intracellular distribution of IP3R. IP3R type 2 and 3 are predominantly expressed in lung endothelial microvasculature. Recruitment of IP3R type 3 into caveolae is required for agonist-induced Ca2+ release from stores. Considering the relatively low intrinsic affinity of IP3 to IP3R type 3 localization of the receptor in the close proximity to the sites of IP3 generation might be critical for IP3-gated release of Ca2+. Therefore, we will test whether EB3 regulates the tethering of ER membrane to caveolae through formation of IP3R3/TRPC1/TRPC4 complex. We will determine the intracellular distribution of the IP3R3 receptor by immunofluorescent staining and by live cell imaging in the time-course of thrombin stimulation. If we will find that EB3 regulates IP3-gated release of Ca2+ by tethering of IP3R3 to caveolae, we will determine whether EB3 facilitates the interaction between IP3R3 and TRPC1/TRPC4.

Example 7

Role of EB3 in the Mechanism of Agonist-Induced IP3R Phosphorylation

IP3R contains 16 potential sites for CaM kinase II (CaMKII) 26-28 and CaMKII-mediated phosphorylation increases receptor sensitivity to IP3. Thr804, a predicted CaMKII phosphorylation site (FIG. 17) is located within 651-1130 region, which is critical for the functional coupling between IP3 binding and channel opening. Therefore, phosphorylation of Thr804 might be important in the mechanism of IP3-induced channel opening. EB3 binds to CaM and it might orchestrate the spatial and temporal activation of CaMKII and phosphorylation of the receptor. To address this idea we will determine whether depletion of EB3 or disruption of interaction between EB3 and IP3R with a specific peptide inhibits IP3R phosphorylation. The level of IP3R phosphorylation will be assessed by autoradiography. We expect that both EB3 depletion and IP3R peptide will reduce the level of IP3R phosphorylation. The sites of phosphorylation will be determined by phosphoproteomic analysis. The endogenous IP3R will be purified from HLMVECs prior and after thrombin treatment using conconavalin A beads. The specificity of CaMKII sites will be determined by comparison of the profiles of phosphorylation obtained with and without CaMKII inhibitors. We will mutate CaMKII sites and will determine their significance in intracellular distribution of IP3R3 and in the mechanism of IP3-gated release of Ca2+.

Another series of experiment will determine whether CaMKII-dependent phosphorylation of IP3R is coupled to binding of the receptor to TRPC1/4 at the plasma membrane. Phosphorylation might release IP3R from growing MT tips and induce its binding to TRPC1/4. The co-localization of CaMKII and IP3R3 is observed in apical region of intestinal enterocytes, pancreatic acinar cells and surface mucous cells. Therefore, the co-distribution of CaMKII and IP3R3 at the luminal surface of endothelial cells might occur. We will first confirm the co-localization of IP3R3 with CaMKII in resting and thrombin-stimulated HLMVECs. We also will determine the interaction between receptor and kinase by FRET analysis. The activity of CaMKII will be assessed using FRET-based biosensor, Camui 33 (obtained from Yasunori Hayashi, Japan). The role of EB3 in spatial activation of CaMKII will be determined using the same approaches.

Example 8

Role of EB3 Interaction with IP3R in the Mechanism of SOC-Evoked Ca2+ Entry

The depletion of ER stores is important mechanism of SOC activation and Ca2+ entry 34-36. Consistently, we found that depletion of EB3 but not EB1 reduces Ca2+ influx. On the premise of our Preliminary Data, we hypothesized that EB3 depletion inhibits thrombin-induced activation of TRPC1 and TRPC4, major SOC channels in endothelial cells. To address this possibility directly, HLMVECs treated with EB3 siRNA or with IP3R3 peptide will be used in the whole cell patch clamp assay to measure thrombin-induced and a La3+-sensitive inward current at −50 mV. We will also evaluate the current-voltage (I-V) relationship (−100 to +100 mV) to demonstrate reversal potential of activated channels. This result will be compared with data obtained in HLMVECs in which IP3R3 will be depleted with siRNA or inhibited with IP3R antagonist, 2-aminoethoxydiphenyl borate (2-APB). Complementary experiments will address whether separate or simultaneous inactivation of TRPC1 and TRPC4 with specific Ab or with siRNA will produce the similar effect on whole cell conductance as compared to depletion of EB3. On the validity of our hypothesis, we predict that EB3 depletion will inhibit Ca2+ entry through TRPC1/4 channels. These experiments will be accompanied by measurements of changes in intracellular Ca2+ concentration by Fura2-AM ratiometric imaging.

Another set of experiments will determine whether depletion of EB3 can inhibit thapsigargin (TG)- or IP3-induced (intracellular delivery my microinjection) activation of SOC and Ca2+ entry. TG inhibits sarco/endoplasmic reticulum Ca2+ ATPase and results in depletion of Ca2+ from ER independently on IP3R activation. Both approaches are expected to induce activation of SOC-evoked Ca2+ entry in control siRNA-treated cells, however depletion of EB3 might inhibit Ca2+ entry only in case of IP3-induced activation of IP3R. This experiments will distinguish between involvement of EB3 in regulating SOC-evoked Ca2+ entry indirectly, through activation of IP3R and directly, if EB3 (or MT dynamics change) has any affect on activation of SOC channel per se. We will evaluate the whole cell conductance and the current-voltage (I-V) relationship to demonstrate the activity of TRPC1/4 channels in these experiments.

Example 9

Role of EB3 Interaction with IP3R in the Mechanism of Increased Endothelial Permeability and Edema Formation We will determine whether interaction between EB3 and IP3R resulting in propagation of Ca2+ signaling potentiates increased permeability response to PAR-1 activation. In this context, we will address the permeability barrier increase in cells and in lungs treated with IP3R blocking peptides. We will assess the endothelial permeability increase by measuring changes in TER and transendothelial albumin fluxes as functional measures of alterations of endothelial barrier. The integrity of AJs and formation of intracellular gaps will be determined by immunostaining, by quantitative analysis of VE-cadherin internalization (using a biotinylation assay), by interaction between VE-cadherin and p120-catenin. On validity of our hypothesis, we expect that inhibition of increase in intracellular Ca2+ concentration will result in reduce permeability response reflected by less intracellular gap formation and more stable VE-cadherin adhesions. Since increased intracellular Ca2+ activates PKCα that mediate disassembly of AJs by phosphorylating p120-catenin, we will determine the level of PKCα activation and the level of p120-catenin phosphorylation on PKCα-specific site, Ser879. To determine whether PAR-1 mediated cell contractility is also inhibited in EB3 depleted cells or in cells pre-treated with IP3R3 peptide we will analyze the level of RhoA and MLCK-L activation. The IP3R3 depleted cells or lung microvascular endothelial cells isolated from IP3R3−/− mice 37 will be used for comparison.

To determine whether interaction between EB3 and IP3R potentiates agonist-induces increase in microvascular permeability and lung edema we will use lung ex vivo model. The mouse perfused lung preparation will be used to determine whether cell-permeant IP3R peptide inhibits PAR-1-mediated increase in lung vascular permeability. The endothelial microvascular permeability will be assessed by measuring capillary filtration coefficient (Kf,c) and pulmonary transvascular 125I-albumin flux after infusion of PAR1 agonist peptide. We will also use IP3R3−/− mice (obtained from Katsuhiko Mikoshiba, Japan) or mice in which IP3R3 will be depleted by siRNA to verify the results obtained with a peptide. If our hypothesis that the interaction between IP3R and EB3 is essential for regulating agonist-induced increase in lung microvascular permeability, we expect that both IP3R peptide and IP3R3−/− will produce comparable results revealing a partial inhibition of increased microvascular permeability in response to PAR-1 activation.

The goal of these studies is to determine the role of EB3 in regulating IP3-gated release of Ca2+ from ER stores. We will determine significance of interaction between EB3 and IP3R in the mechanism of IP3R phosphorylation and ER translocation to the apical plasmalemma. We anticipate based on our hypothesis that interaction between EB3 and IP3R provides a control-point of IP3R activation. On validity of our hypothesis, we predict that disruption of EB3 interaction with IP3R will inhibit release of Ca2+ from ER stores and will abrogate the increased permeability response in cells culture and in lungs. We will interrogate the following mechanistic models that EB3/IP3R interaction regulates IP3-gated release of Ca2+1) by tethering of IP3R3 to the caveolae, to the close proximity of IP3 generation and 2) by facilitating IP3R3 phosphorylation by CaMKII. Thus, the cell culture experiments, together with lung microvessel studies will identify the mechanism by which EB3 regulates IP3R3 activity. We do not foresee problems in regards to being able to draw novel conclusions from these studies on the basis of testing the hypotheses. All proposed techniques are established in our laboratory or in laboratory of co-Investigators and therefore feasible.

MT cytoskeleton plays important role in maintenance of endothelial barrier in resting cells and provides the mechanism for potentiating increased endothelial permeability as mediated by pro-inflammatory stimuli. EB3, a MT end binding protein, which regulates MT dynamics by promoting persistent MT growth and therefore, EB3 anti-catastrophe activity might be a primary mechanism controlling re-organization of MT cyto skeleton and the loss of endothelial barrier function during inflammatory diseases such as acute lung injury (ALI) and Adult Respiratory Distress Syndrome (ARDS). The proposed studies will address the roles of EB3 in regulating IP3-gated release of Ca2+ from ER stores in response to PAR-1 activation in the mechanism endothelial vascular permeability and edema formation. We will define the potentially important interaction between EB3 and IP3R3 in the mechanism of organization and propagation of Ca2+ waves that mediates increased endothelial permeability though PKCα-mediated AJ disassembly and RhoA/MLCK-L-driven acto-myosin contractility.

Example 10

Effect of Truncation of IP$_3$R$_3$ Peptide on Binding to EB3

Computational in silico modeling was used to estimate the energetic contribution to the binding free energy provided by each residue in the KFARLWTEIPTAIT peptide (SEQ ID NO: 1). A truncated variants of the amino acid sequence: KFARLWTEIPTAIT (SEQ ID NO: 1) was docked into EB3 interface and the free energy of the interaction was computed (Table 1). The data demonstrate that Thr-x-Ile-Pro has the lowest binding energy and flanking amino acids play a critical role in stabilizing the interaction between EB3 and peptide.

TABLE 1

Computed changes in binding free energy after truncation of amino acid residues which surround Thr-x-Ile-Pro motif of IP$_3$R$_3$ peptide

| Peptide Sequence | Free Energy Binding (-kcal/mole) |
| --- | --- |
| KFARLWTEIPTAIT (IP$_3$R$_3$ peptide) | -68.882 |
| FARLWTEIPTAIT | -68.809 |
| RLWTEIPTAIT | -46.571 |
| LWTEIPTAIT | -54.443 |
| WTEIPTAIT | -42.886 |
| TEIPTAIT | -37.16 |
| TEIPTAI | -39.337 |
| TEIPTA | -41.234 |
| TEIPT | -34.5 |
| FARLWTEIPTAI | -51.42 |
| TEIP | -45.071 |
| RTEIPTI | -49.74 |
| FRTEIPTI | -40.728 |
| FTKIPTI | -55.469 |
| KFARTKIPTAIT | -57.32 |
| FARTEIPTAI | -33.415 |
| KFARTEIPTAIT | -55.736 |

Example 11

Structure-Based Design of End Binding Inhibitory Peptide (EBIN)

End Binding Inhibitory peptide, namely EBIN, was designed based on computational in silico alanine-scanning and fully-flexible docking of IPR peptide to the EB binding pocket (Tables 2 and 3). Binding free energy (ΔG) was used to determine a contribution of each residue in stabilization of interaction of the peptide with EB protein.

The following criteria were used:
ΔG value≥1=Stabilizing residue
ΔG value≥-1=Destabilizing residue
ΔG value<-1 to 0 to <1=Neutral residue
Alanine scanning reveals stabilizing (with a positive binding energy of 0.50 Kj/mole or more; shown in black) and destabilizing (with a negative binding energy of -1, shown in blue) residues.

TABLE 2

Computed changes in binding free energy after mutating each amino acid residue of IP$_3$R$_3$ peptide for alanine: $K_1F_2A_3R_4L_5W_6T_7E_8I_9P_{10}T_{11}A_{12}I_{13}T_{14}$

| Amino acid | ΔG |
| --- | --- |
| K1 | 0.25 |
| F2 | 0.52 |
| R4 | 0.01 |
| L5 | -1.03 |
| W6 | -1.08 |
| T11 | 0.91 |
| I13 | 1.33 |
| T14 | 0.40 |

TABLE 3

Computed changes in binding free energy after mutating each amino acid residue of EBIN for alanine.

| Amino acid | ΔG |
| --- | --- |
| F1 | 1.64 |
| T2 | 1.07 |
| E3 | 0.02 |
| I4 | 0.68 |
| T11 | 0.98 |
| I7 | 0.94 |

Figure 12:
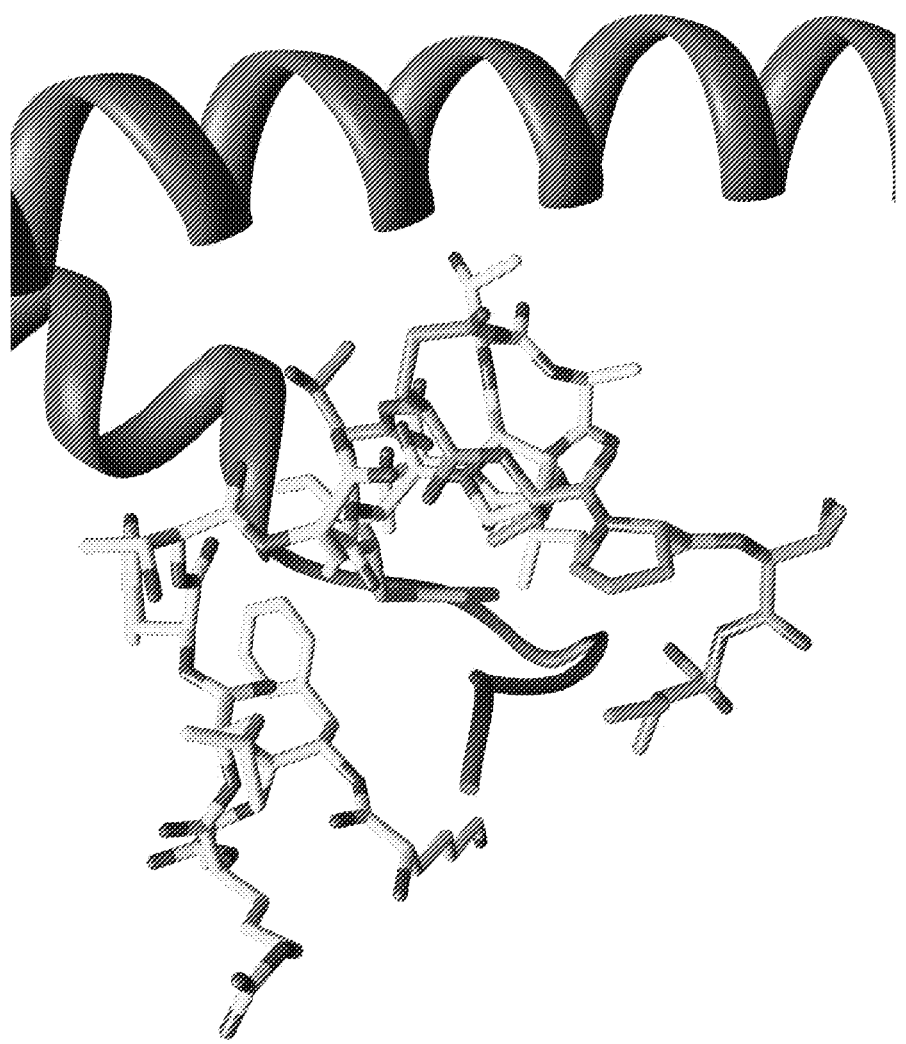
FIG. 12 shows a ribbon representation of EB3 (magenta) in the complex with EBIN (SEQ ID NO: 3) (Green stick) and IP$_3$R$_3$ peptide (Yellow stick) (SEQ ID NO: 1). The computed binding energy is −68.882 and −60.251 for IPR and EBIN, respectively.

As a result, the 14 amino acid IPR peptide was reduced to the 7 amino acid End Binding Inhibitory peptide (EBIN; FTEIPTI (SEQ ID NO: 3). FIG. 12 demonstrates the interaction between EB3 and EBIN. Similarly to IP$_3$R$_3$ (is shown in yellow stick in FIG. 12), EBIN binds to hydrophobic grove between EB acidic tail and coil-coiled domain. The calculated energy binding of EBIN to EB3 is -60.251 kcal/mol, which is similar to the energy binding between IPR and EB3. Threonine at position 2 of EBIN plays a critical role in binding to the EB3 interface because mutation of this residue to alanine completely abolishes the binding. Therefore, a single amino-acid mutation T→A peptide, FAEIPTI (SEQ ID NO: 4), was used as a loss-of-binding control.

Example 12

Figure 13:
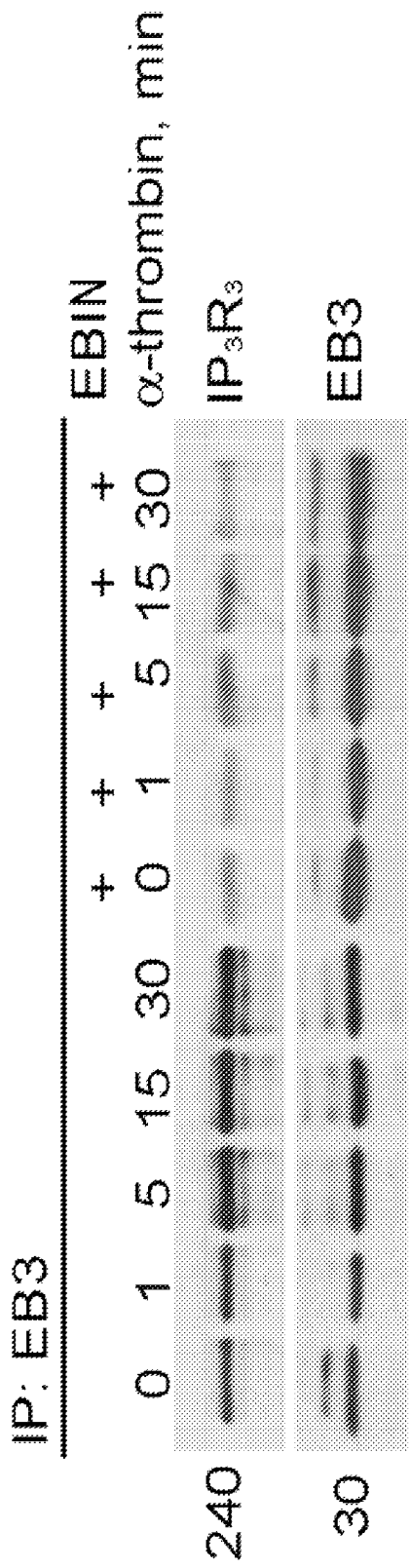
FIG. 13 shows that EBIN (SEQ ID NO: 3) inhibits interaction between IP3R3 and EB3. HPAECs pretreated with 1 μM AP-EBIN or control peptide (AP) were challenged with 50 nM thrombin. The interaction between EB3 and IP$_3$R$_3$ was analyzed at different time-points after thrombin stimulation. EB3 was immune-precipitated with specific Abs and resulted precipitates were probed for EB3 and IP$_3$R$_3$. EBIN markedly reduced the EB3-IP$_3$R$_3$ interaction basally and after thrombin treatment.
Figure 14:
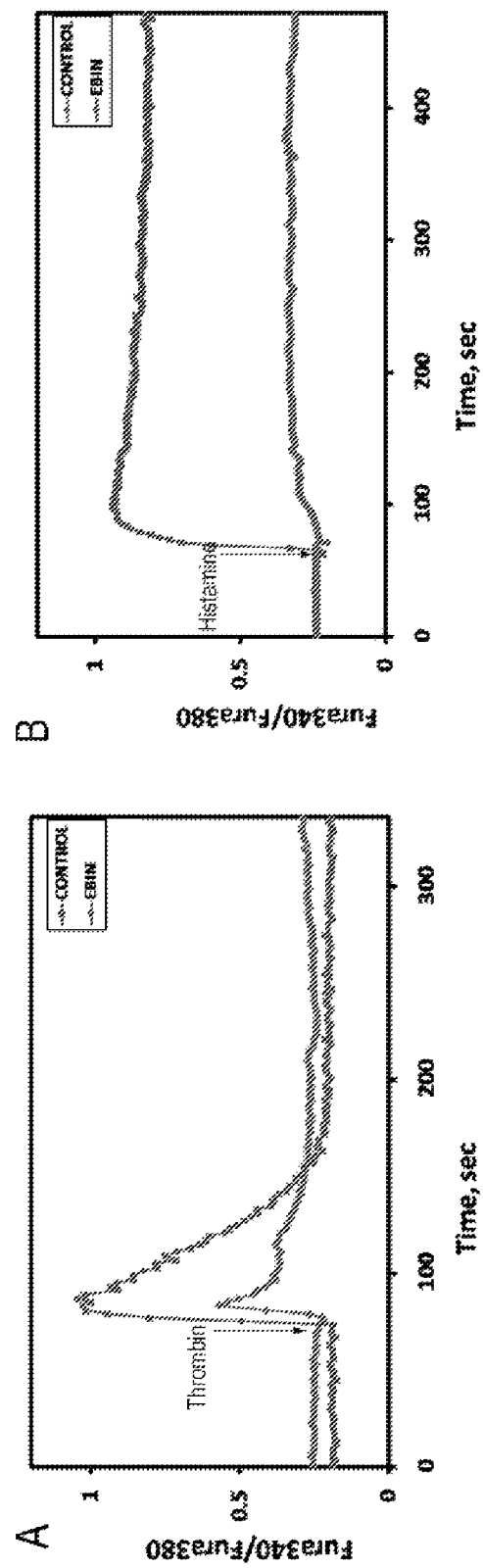
FIG. 14 shows that Myr-EBIN (SEQ ID NO: 3) mitigates agonist-induced increase in intracellular calcium. [Ca2+]i transient after stimulation of HPAEC monolayers with 50 nM thrombin (A) or 90 μM histamine (B). Mean value; n=20 cells. Arrow, time of stimulation. Note that EBIN (blue tracers) markedly reduced [Ca$^{2+}$]i transient in control peptide (loss-of-binding; FAEIPTI (SEQ ID NO: 4)) treated cells (red tracers).

EBIN Inhibits EB3/IP$_3$R$_3$ Interaction and Attenuates Intracellular Calcium Flux in Response to Pro-Inflammatory Mediators To determine the inhibitory properties of EBIN in cells, Human Pulmonary Aorta Endothelial Cell (HPAECs) monolayers pretreated with EBIN or with a control peptide at the concentration of 1 μM were challenged with thrombin. The interaction between EB3 and IP$_3$R$_3$ receptor was analyzed using a Western Blot analysis. As demonstrated in FIG. 13, EBIN treatment attenuated basal and thrombin-induced interaction between EB3 and IP3R3. Consistently with the idea of the role of EB3 in modulating the IP$_3$R$_3$'s responsiveness to IP3, EBIN significantly inhibited the intracellular calcium flux in response to thrombin and histamine. FIG. 14 demonstrates changes in 340/380 (bound/free Fura-2M) ratio in HPAECs pre-treated with 1 μM Myr-EBIN or control peptide (FAEIPTI) (SEQ ID NO: 4) and challenge with 50 nM thrombin or 90 μM histamine. EBIN but not a control peptide mitigated agonist-induced increase in intracellular calcium. [Ca2-F]i transient after stimulation of HPAEC monolayers with pro-inflammatory cytokines.

Figure 15:
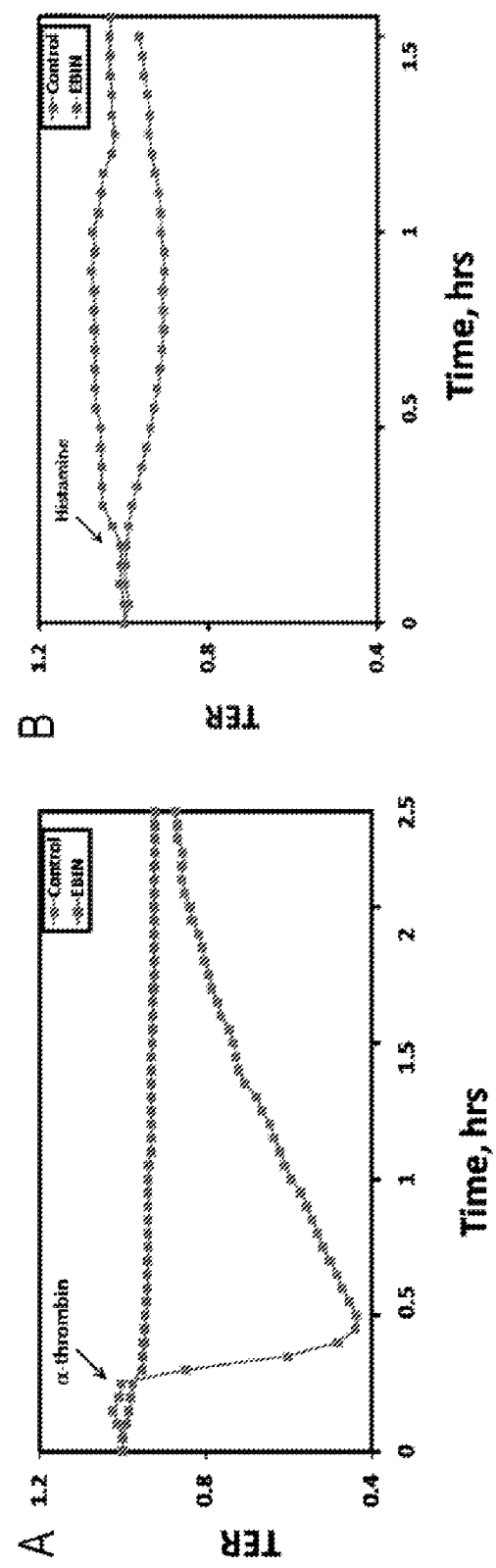
FIG. 15 shows that EBIN (SEQ ID NO: 3) attenuates agonist-induced endothelial paracellular hyperpermeability. Changes in transendothelial electrical resistance (TER) of HPAEC monolayers in response to 50 nM a-thrombin (A) and 50 μM histamine (B). TER values were normalized to the baseline resistance. Myr-EBIN (red plot) prevented cell shape change and paracellular hyperpermeability in response to thrombin and histamine as it observed in control peptide treated cells (blue plot).

To determine EBIN effect on cell shape change and paracellular permeability, trans-endothelial resistance of HPAEC monolayers were measured. FIG. 15 demonstrates that EBIN, but not with a loss-of-binding peptide, inhibited cell shape change and paracellular hyperpermeability of HPAEC monolayers in response to both pro-inflammatory mediators. These results demonstrate that the barrier protective effect of EBIN is associated with inhibition of calcium signaling and cell shape change of endothelium.

Example 13

EBIN Inhibits NO Production and Histamine-Induced Vasodilation in Mice

Figure 16:
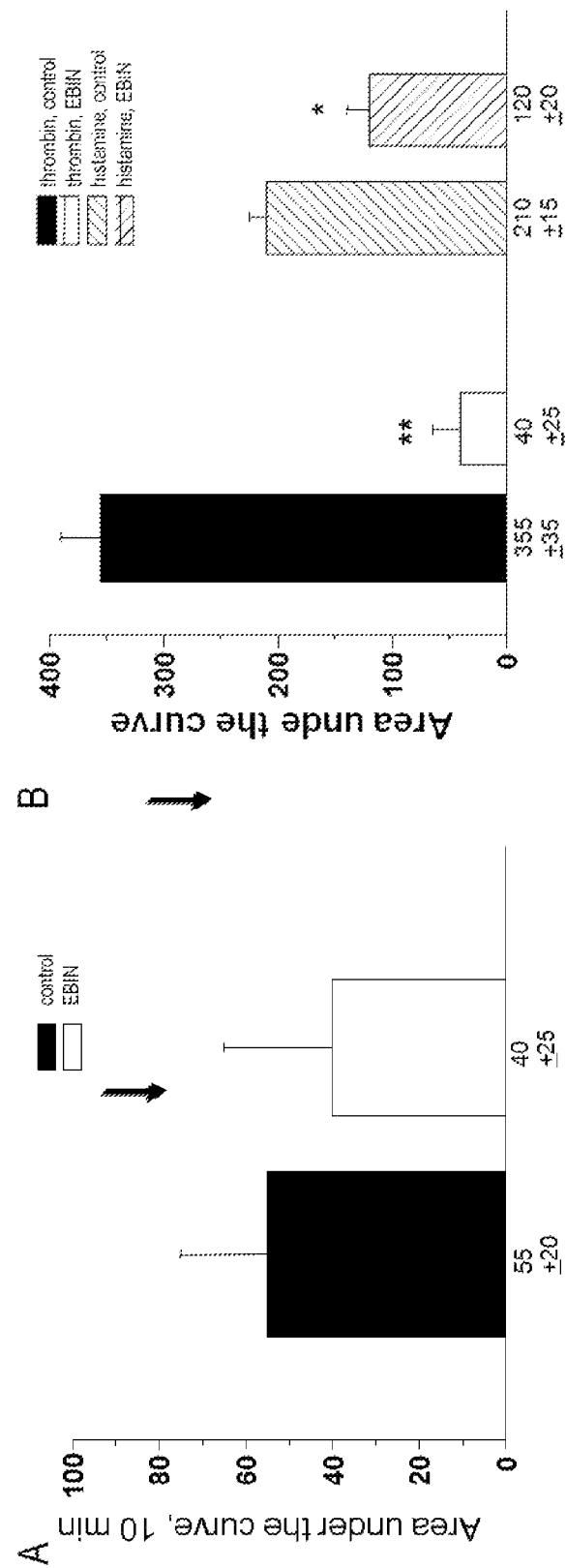
FIG. 16 shows that EBIN (SEQ ID NO: 3) inhibits agonist-induced NO production. HPAECs were pretreated with control peptide (loss-of-activity) or Myr-EBIN and basal (A, in response to addition of L-arginin) and agonist-induced (B, thrombin and histamine) NO production was measured for the first 20 min stimulation. EBIN did not affect basal NO level but significantly attenuated agonist-induced NO. *, p<0.01 and **, p<0.01.
Figure 17:
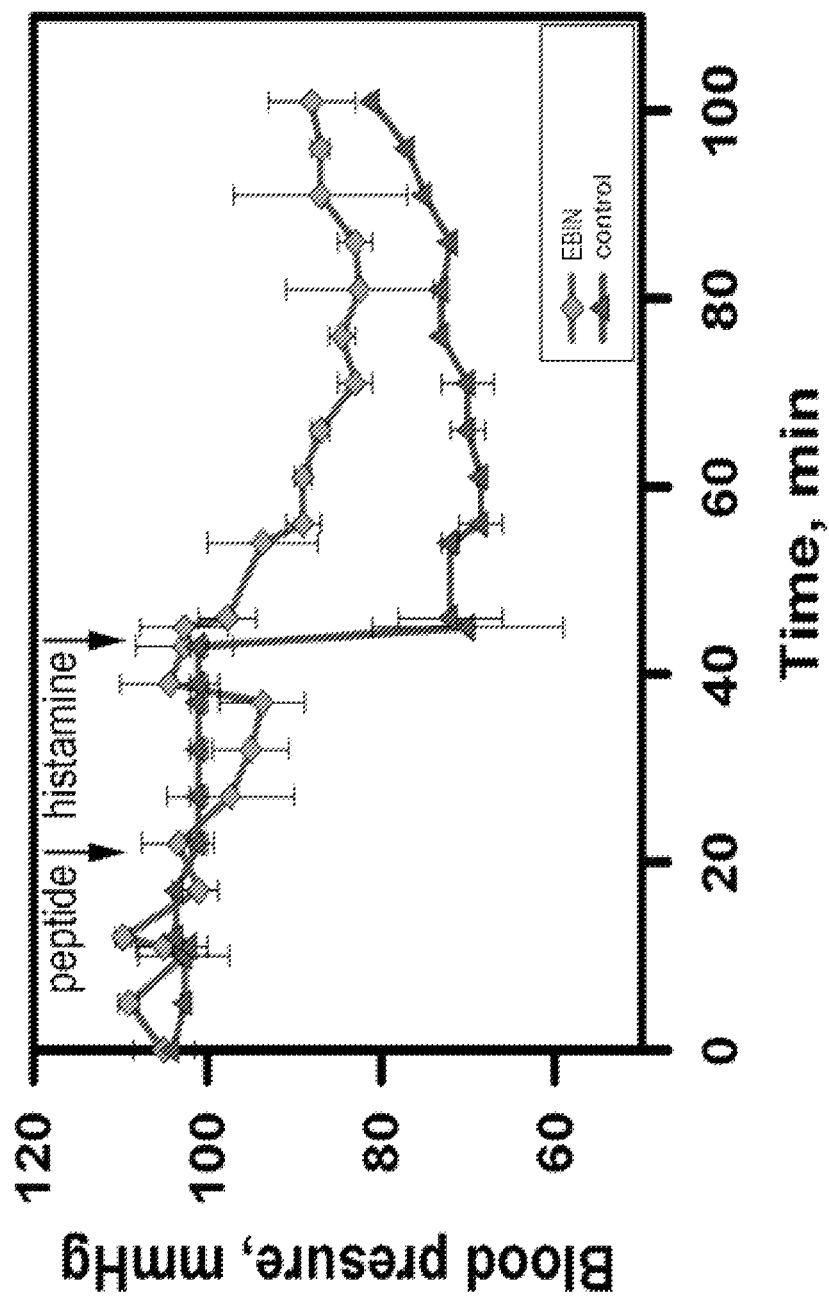
FIG. 17 shows that EBIN (SEQ ID NO: 3) prevents histamine-induced vasodilation in vivo. Awake Blood Pressure Measurement in Mice-Mice were anesthetized and surgically prepared for placement of arterial (carotid) and venous (external jugular) catheters. One hour after surgery the blood pressure was monitored directly using a pressure transducer. Subsequent intravenous (i.v.) injections of AP-EBIN peptide (1 μM/kg body weight; green) or control AP peptide (red) and histamine (10 mg/kg body weight) were performed through jugular vein catheter; the arrow indicates the time of injection. Note, EBIN had no effect on baseline blood pressure and prevented blood pressure drop in response to histamine. n=6 mice/group.

The activity of nitric oxide synthase 3(eNOS), an endothelial-specific enzyme that produces NO, is regulated by calcium signaling, particularly, through eNOS interaction with calmodulin, and is a known cause of hyperpermeability of endothelial barrier during inflammation. Because EBIN inhibits calcium signaling it was postulated that the barrier-protective effect of EBIN, in part, is due to inhibition of eNOS. Therefore, the effect of EBIN on basal and agonist-induced production of NO was measured. NO formation was measured using porphyrinic NO electrodes coupled to a FAS1 femtostat and a personal computer with electrochemical software (Gamry Instruments). The electrode current, which is proportional to NO concentration, was measured as a function of time. Interestingly, EBIN showed no effect on basal NO production, suggesting that it does not inhibit constitutive eNOS activity. EBIN, however, significantly attenuated agonist-induced NO production (FIG. 16). Consistently with these results, i.v. injection of AP-EBIN in mice showed no effect on the systolic blood pressure, however EBIN significantly inhibited histamine-induced vasodilation (FIG. 17). These data are in agreement with data obtained in cell culture experiments. These results demonstrate that EBIN attenuates vasodilation by inhibiting NO generation in response to histamine.

Example 14

Figure 18:
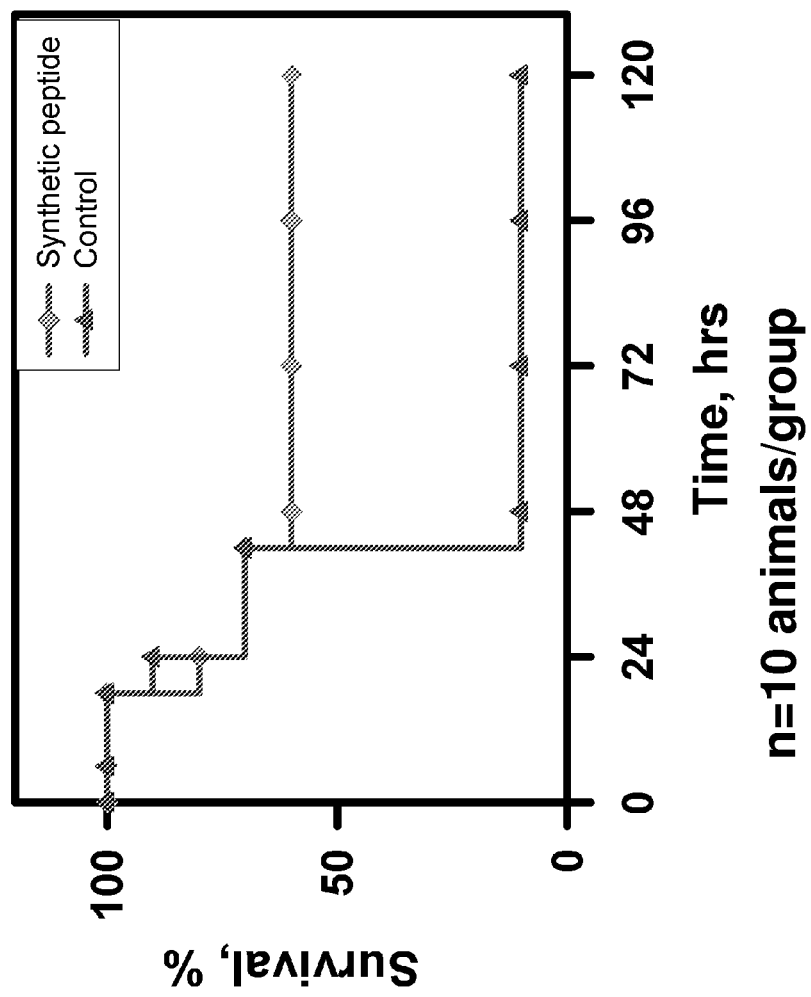
FIG. 18 shows EBIN (SEQ ID NO: 3) prevents lethality from LPS-induced sepsis. Mice treated with EBIN experience reduced mortality in the 120-hr period after LPS injection at LD90 dose (50 mg/kg *E. Coli* LPS 0111:B4). Male CD1 mice were challenged by intraperitoneal (i.p.) injection of LD90 doses of LPS. The experimental and control groups received retro-orbital, intravenous (i.v.) injection of EBIN attached to the C-terminus of cell permeant antennapedia peptide (AP) or AP alone at a concentration of 1 microM/kg. Mice were injected tree times, 30 minutes prior to and 1 hr and 24 hrs after LPS administration. Mice were anesthetized prior to retro-orbital injection with a mixture of ketamine (10 mg/ml), xylazine (0.25 mg/ml), and acepromazine (0.25 mg/ml).
Figure 19:
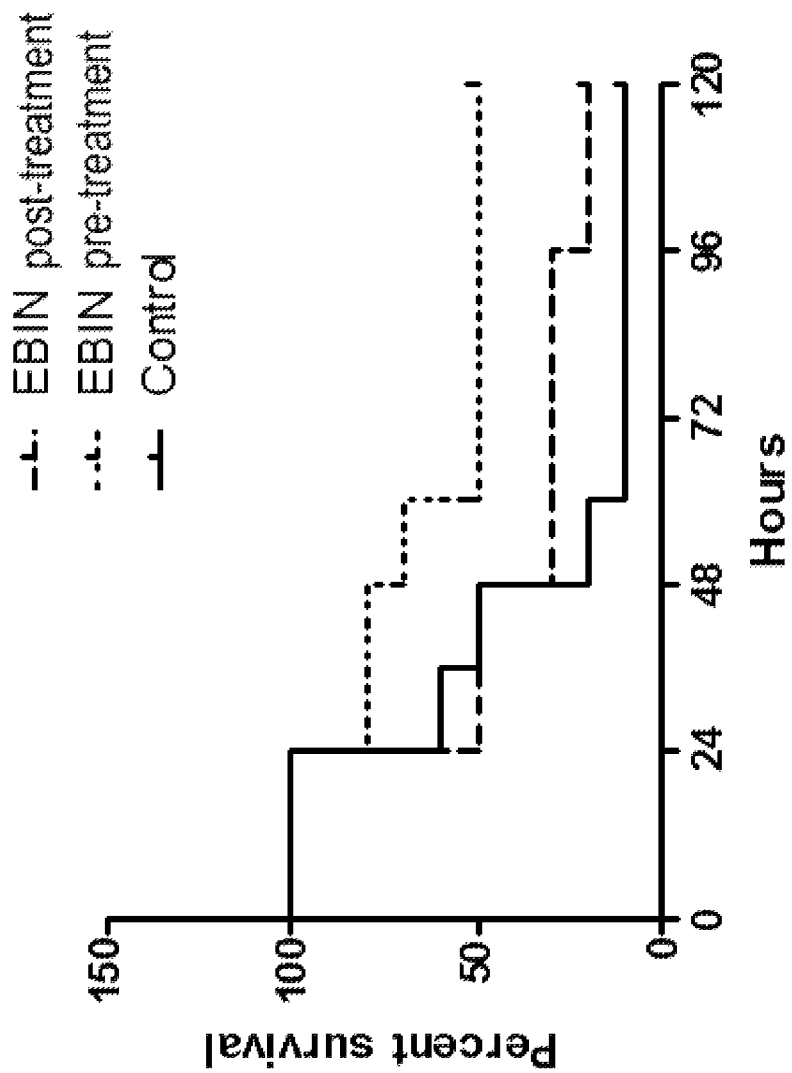
FIG. 19 compares the effect of pre- and post treatment with EBIN (SEQ ID NO: 3) on lethality from LPS-induced sepsis. Mice treated with EBIN experience reduced mortality in the 120-hr period after LPS injection at LD90 dose (50 mg/kg *E. Coli* LPS 0111:B4). Male CD1 mice were challenged by intraperitoneal (i.p.) injection of LD90 doses of LPS. The experimental and control groups received tail vein (i.v.) injection of Myr-EBIN 30 min prior (pre-treatment) or 30 min after (post-treatment) LPS or Myr-control loss-of-binding peptide at a concentration of 1 microM/kg. Pre-treatment group, mice were injected tree times, 30 minutes prior to and 1 hr and 24 hrs after LPS administration; treatment group, mice were injected two times, 30 minutes and 24 hrs after LPS administration. Mice were anesthetized prior to retro-orbital injection with a mixture of ketamine (10 mg/ml), xylazine (0.25 mg/ml), and acepromazine (0.25 mg/ml). Post-treatment with EBIN shows some but not significant improvement of the survival.

EBIN Prevents Lethality in LPS-Induced Sepsis and Vascular Leak Following an Anaphylaxis The effect of EBIN on mortality rate from LPS-induced sepsis was determined. Mice received i.v. retro-orbital injection of AP-EBIN or AP control peptide, 30 minutes prior to and 1 hr after LPS administration at LD90 dose. Mice treated with EBIN demonstrated marked improvement in survival rate of control groups (FIG. 18). Furthermore, it was determined whether post-treatment of EBIN also shows any protective effect. In this experiment, Myr-EBIN was injected in tail vein 30 min and 24 hrs after LPS challenged. As shown in FIG. 19, post-treatment with EBIN lead to insignificant improvement in survival rate as compared to control group (loss-of-binding peptide). Consistently with previous results with Ap-EBIN, pre-treatment with Myr-EBIN demonstrated significant increase ($p<0.05$) in survival rate (FIG. 19). It is concluded that administration of EBIN prior to systemic inflammation has much higher beneficial outcome.

Figure 20:
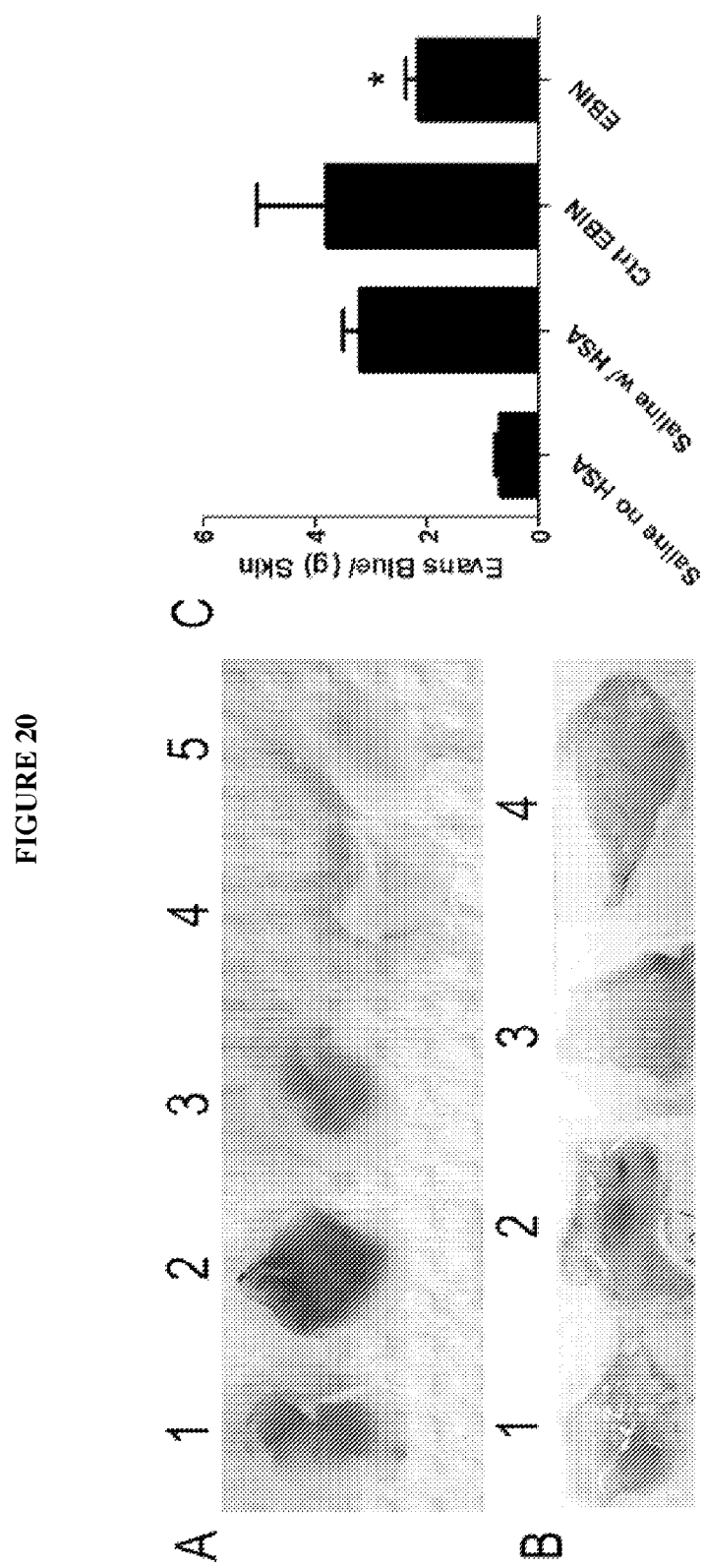
FIG. 20 shows that EBIN (SEQ ID NO: 3) prevents subcutaneous vascular leak following an IgE-mediated anaphylactic reaction. Mice received intradermal injection of IgE-HSA in the ear (A) and back (B) and 24 hr later, iv injection of Evans Blue and HSA (1-3) or saline (4-5). Groups 1 and 4 received saline, 2—control peptide (loss-of-binding) and 3 and 5—Myr-EBIN iv injection (1 μM/kg) 30 min prior to HSA. Note, injection of HSA resulted in local vascular leak, which was significantly attenuated by EBIN (group 3). C. Bar plot demonstrating the vascular leak of Evans Blue. Evans Blue was extracted from ear tissue and Evans Blue concentration was measured at A=620 nm and normalized to the tissue weight. *, p<0.05, n=6 mice/group.

Airway microvascular hyperpermeability, the result of elevated plasma VEGF, is one of the critical factors contributing to abnormal airway function in patients with classic asthma and its cough variant. Because acute allergic asthmatic response is mainly due to IgE-mediated hypersensitivity, we also determined whether EBIN protects from subcutaneous vascular leak following an IgE-mediated anaphylactic reaction. FIG. 20 shows that intravenous injection of EBIN but not the control loss-of-binding peptide significantly attenuates subcutaneous vascular leak (size and intensity of Evan Blue-positive area) in the ear (high vascularization, A) and back (low vascularization, B). These date indicate that EBIN might be effectively used to improve the lung function and overall health of patients with chronic or acute forms of allergic asthma, and curtail the asthmatic inflammatory response.

The invention claimed is:

1. A conjugated peptide comprising an amino acid sequence selected from the group consisting of KFARLW-TEIPTAIT (SEQ ID NO: 1) and FTEIPTI (SEQ ID NO: 3), wherein the conjugated peptide is linked to a carrier peptide or myristoyl group.

2. The peptide of claim 1, wherein the peptide is linked to a carrier peptide.

3. The peptide of claim 2, wherein the carrier peptide is antennapedia peptide (AP).

4. The peptide of claim 1, wherein the peptide is myristoylated.

5. A pharmaceutical formulation comprising a pharmaceutically acceptable excipient and the conjugated peptide of claim 1.

6. A method of treating a disease or condition selected from the group consisting of: anaphylaxis-mediated vascular leakage, inflammation-mediated vascular leakage and IgE-mediated anaphylaxis, comprising administering to a patient in need thereof a composition comprising the conjugated peptide of claim 1.

7. The method of claim 6, wherein the anaphylaxis is selected from the group consisting of allergen-induced and a non-allergic anaphylactoid reaction.

8. The method of claim 7, wherein the non-allergic anaphylactoid reaction is due to a contrast dye.

9. A conjugated peptide consisting of the amino acid sequence of SEQ ID NO: 1 or SEQ ID NO: 3, linked to a carrier peptide or a myristoyl group.

10. The conjugated peptide of claim 9, wherein the carrier peptide is antennapedia peptide (AP).

11. The conjugated peptide of claim 9, wherein the peptide is linked to a carrier peptide.

12. The conjugated peptide of claim 9, wherein the peptide is myristoylated.

13. A pharmaceutical formulation comprising a pharmaceutically acceptable excipient and the conjugated peptide of claim 9.

* * * * *

SEQUENCE LISTING

```
<160> NUMBER OF SEQ ID NOS: 8

<210> SEQ ID NO 1
<211> LENGTH: 14
<212> TYPE: PRT
<213> ORGANISM: Artificial sequence
<220> FEATURE:
<223> OTHER INFORMATION: EB binding peptide

<400> SEQUENCE: 1

Lys Phe Ala Arg Leu Trp Thr Glu Ile Pro Thr Ala Ile Thr
1               5                   10

<210> SEQ ID NO 2
<211> LENGTH: 14
<212> TYPE: PRT
<213> ORGANISM: Artificial sequence
<220> FEATURE:
<223> OTHER INFORMATION: EB binding peptide
```

```
<400> SEQUENCE: 2

Lys Phe Ala Arg Leu Trp Ala Glu Ile Pro Thr Ala Ile Thr
1               5                   10

<210> SEQ ID NO 3
<211> LENGTH: 7
<212> TYPE: PRT
<213> ORGANISM: Artificial sequence
<220> FEATURE:
<223> OTHER INFORMATION: EB binding peptide

<400> SEQUENCE: 3

Phe Thr Glu Ile Pro Thr Ile
1               5

<210> SEQ ID NO 4
<211> LENGTH: 7
<212> TYPE: PRT
<213> ORGANISM: Artificial sequence
<220> FEATURE:
<223> OTHER INFORMATION: EB non-binding control peptide

<400> SEQUENCE: 4

Phe Ala Glu Ile Pro Thr Ile
1               5

<210> SEQ ID NO 5
<211> LENGTH: 21
<212> TYPE: PRT
<213> ORGANISM: Homo sapiens

<400> SEQUENCE: 5

Val Thr Pro Val Lys Tyr Ala Arg Leu Trp Ser Glu Ile Pro Ser Glu
1               5                   10                  15

Ile Ala Ile Asp Asp
            20

<210> SEQ ID NO 6
<211> LENGTH: 21
<212> TYPE: PRT
<213> ORGANISM: Homo sapiens

<400> SEQUENCE: 6

Val Val Pro Val Arg Tyr Ala Arg Leu Trp Thr Glu Ile Pro Thr Lys
1               5                   10                  15

Ile Thr Ile His Glu
            20

<210> SEQ ID NO 7
<211> LENGTH: 21
<212> TYPE: PRT
<213> ORGANISM: Homo sapiens

<400> SEQUENCE: 7

Val Thr Pro Val Lys Phe Ala Arg Leu Trp Thr Glu Ile Pro Thr Ala
1               5                   10                  15

Ile Thr Ile Lys Asp
            20

<210> SEQ ID NO 8
<211> LENGTH: 4
<212> TYPE: PRT
<213> ORGANISM: Artificial
```

```
<220> FEATURE:
<223> OTHER INFORMATION: EB binding motif
<220> FEATURE:
<221> NAME/KEY: Xaa
<222> LOCATION: (1)..(1)
<223> OTHER INFORMATION: Ser or Thr
<220> FEATURE:
<221> NAME/KEY: Xaa
<222> LOCATION: (2)..(2)
<223> OTHER INFORMATION: Any amino acid

<400> SEQUENCE: 8

Xaa Xaa Ile Pro
1
```